US011180737B2

(12) United States Patent
Kawaoka et al.

(10) Patent No.: US 11,180,737 B2
(45) Date of Patent: Nov. 23, 2021

(54) GENERATION OF INFECTIOUS INFLUENZA VIRUSES FROM VIRUS-LIKE PARTICLES

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

(21) Appl. No.: 16/547,262

(22) Filed: Aug. 21, 2019

(65) Prior Publication Data

US 2020/0263142 A1 Aug. 20, 2020

Related U.S. Application Data

(62) Division of application No. 15/247,006, filed on Aug. 25, 2016, now Pat. No. 10,494,613.

(60) Provisional application No. 62/211,125, filed on Aug. 28, 2015.

(51) Int. Cl.
*C12N 7/00* (2006.01)
*A61K 39/12* (2006.01)
*A61K 39/00* (2006.01)

(52) U.S. Cl.
CPC ................ *C12N 7/00* (2013.01); *A61K 39/12* (2013.01); *A61K 2039/5254* (2013.01); *C12N 2760/16123* (2013.01); *C12N 2760/16134* (2013.01); *C12N 2760/16151* (2013.01); *C12N 2760/16152* (2013.01); *C12N 2760/16223* (2013.01); *C12N 2760/16234* (2013.01); *C12N 2760/16251* (2013.01); *C12N 2760/16252* (2013.01)

(58) Field of Classification Search
None
See application file for complete search history.

(56) References Cited

U.S. PATENT DOCUMENTS

| | | | |
|---|---|---|---|
| 5,166,057 | A | 11/1992 | Palese et al. |
| 5,786,199 | A | 7/1998 | Palese |
| 5,854,037 | A | 12/1998 | Palese et al. |
| 6,001,634 | A | 12/1999 | Palese et al. |
| 6,271,011 | B1 | 8/2001 | Lee et al. |
| 6,843,996 | B1 | 1/2005 | Parkin et al. |
| 7,176,021 | B2 | 2/2007 | Kawaoka |
| 7,226,774 | B2 | 6/2007 | Kawaoka |
| 7,585,657 | B2 | 9/2009 | Kawaoka |
| 7,723,094 | B2 | 5/2010 | Kawaoka et al. |
| 8,298,805 | B2 | 10/2012 | Kawaoka |
| 8,597,661 | B2 | 12/2013 | Kawaoka et al. |
| 9,101,653 | B2 | 8/2015 | Kawaoka et al. |
| 10,494,613 | B2 | 12/2019 | Kawaoka et al. |
| 10,513,692 | B2 | 12/2019 | Kawaoka et al. |
| 2004/0002061 | A1 | 1/2004 | Kawaoka |
| 2004/0132164 | A1 | 7/2004 | Doyle et al. |
| 2004/0241139 | A1 | 12/2004 | Hobom et al. |
| 2005/0037487 | A1 | 2/2005 | Kawaoka et al. |
| 2006/0166321 | A1 | 7/2006 | Kawaoka et al. |
| 2007/0141699 | A1 | 6/2007 | Kawaoka |
| 2007/0231348 | A1 | 10/2007 | Kawaoka et al. |
| 2008/0009031 | A1 | 1/2008 | Kawaoka |
| 2008/0292658 | A1 | 11/2008 | De Wit et al. |
| 2009/0311669 | A1 | 12/2009 | Kawaoka |
| 2009/0324640 | A1 | 12/2009 | Kawaoka et al. |
| 2013/0230552 | A1 | 9/2013 | Kawaoka et al. |
| 2015/0166967 | A1 | 6/2015 | Kawaoka et al. |
| 2015/0307851 | A1 | 10/2015 | Kawaoka et al. |
| 2017/0058265 | A1 | 3/2017 | Kawaoka et al. |
| 2020/0263143 | A1 | 8/2020 | Kawaoka et al. |

FOREIGN PATENT DOCUMENTS

| | | | |
|---|---|---|---|
| CA | 2379012 | A1 | 1/2001 |
| CA | 2816242 | C | 1/2019 |
| CN | 103540614 | B | 2/2018 |
| EP | 1201760 | A1 | 5/2002 |
| EP | 1572910 | B1 | 12/2015 |
| EP | 2747778 | B1 | 12/2017 |
| EP | 3009507 | B1 | 6/2020 |
| JP | 07-203958 | | 8/1995 |
| JP | 2003-528570 | A | 9/2003 |
| JP | 2006525815 | A | 11/2006 |
| JP | 2007-525175 | A | 9/2007 |
| JP | 2007-529997 | A | 11/2007 |
| JP | 2008520248 | A | 6/2008 |
| JP | 2009-511084 | A | 3/2009 |
| JP | 2011-530295 | A | 12/2011 |
| JP | 2017197555 | A | 11/2017 |
| JP | 2020114250 | A | 7/2020 |
| KR | 101113432 | B1 | 2/2012 |
| WO | WO-0060050 | A2 | 10/2000 |
| WO | WO-0179273 | A2 | 10/2001 |
| WO | WO-03068923 | A2 | 8/2003 |

(Continued)

OTHER PUBLICATIONS

"U.S. Appl. No. 16/694,748, Preliminary Amendment filed May 8, 2020", 7 pgs.

(Continued)

*Primary Examiner* — Benjamin P Blumel

(74) *Attorney, Agent, or Firm* — Schwegman Lundberg & Woessner, P.A.

(57) ABSTRACT

Compositions and methods to prepare influenza virus-like particles (VLPs) are provided.

13 Claims, No Drawings

Specification includes a Sequence Listing.

(56) References Cited

FOREIGN PATENT DOCUMENTS

| WO | WO-2006051069 A2 | 5/2006 |
|---|---|---|
| WO | WO-2008147496 A2 | 12/2008 |
| WO | WO-2008147496 A3 | 12/2008 |
| WO | WO-2008156681 A2 | 12/2008 |
| WO | WO-2013032942 A1 | 3/2013 |
| WO | WO-2013032942 A9 | 3/2013 |
| WO | WO-2013087945 A2 | 6/2013 |
| WO | WO-2013/148302 A1 | 10/2013 |
| WO | WO-2017040203 A1 | 3/2017 |

OTHER PUBLICATIONS

"European Application Serial No. 16778485.9, Communication Pursuant to Article 94(3) EPC dated May 25, 2020", 5 pgs.
"Japanese Application Serial No. 2018-510751, Response filed Apr. 17, 2020 to Examiners Decision of Final Refusal dated Dec. 17, 2019", (w/ English Translation of Claims), 7 pgs.
"European Application Serial No. 16778485.9, Response filed Oct. 5, 2020 to Communication Pursuant to Article 94(3) EPC dated May 25, 2020", 14 pgs.
"U.S. Appl. No. 14/699,213, Notice of Allowance dated Jul. 30, 2019", 8 pgs.
"U.S. Appl. No. 14/699,213, PTO Response to Rule 312 Communication dated Nov. 19, 2019", 2 pgs.
"U.S. Appl. No. 14/699,213, Response filed Apr. 11, 2019 to Non-Final Office Action dated Jan. 11, 2019", 13 pgs.
"U.S. Appl. No. 15/247,006, Notice of Allowance dated Oct. 8, 2019", 7 pgs.
"Brazilian Application Serial No. PI0307679-2, Office Action dated May 13, 2019", (w/ English Translation), 17 pgs.
"Brazilian Application Serial No. PI0307679-2, Response filed Aug. 16, 2019 to Office Action dated May 13, 2019", (w/ English Translation of Claims), 29 pgs.
"European Application Serial No. 15197386.4, Communication Pursuant to Article 94(3) EPC dated Jun. 19, 2019", 4 pgs.
"European Application Serial No. 15197386.4, Response filed Aug. 27, 2019 to Communication Pursuant to Article 94(3) EPC dated Jun. 19, 2019", 61 pgs.
"European Application Serial No. 16778485.9, Communication Pursuant to Article 94(3) EPC dated Aug. 22, 2019", 5 pgs.
"European Application Serial No. 16778485.9, Response filed Dec. 19, 2019 to Communication Pursuant to Article 94(3) EPC dated Aug. 22, 2019", 20 pgs.
"Japanese Application Serial No. 2003-315106, Notice of Allowance dated Jan. 5, 2010", (w/ English Translation), 5 pgs.
"Japanese Application Serial No. 2017-111526, Office Action dated May 14, 2019", (w/ English Translation), 6 pgs.
"Japanese Application Serial No. 2018-510751, Examiners Decision of Final Refusal dated Dec. 17, 2019", w/ English Translation, 10 pgs.
"Japanese Application Serial No. 2018-510751, Notification of Reasons for Refusal dated Mar. 13, 2019", (w/ English Translation), 14 pgs.
"Japanese Application Serial No. 2018-510751, Response filed Aug. 9, 2019 to Notification of Reasons for Refusal dated Mar. 13, 2019", (w/ English Translation of Claims), 24 pgs.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2), Academic Press, Orlando, US, (Sep. 30, 2000), 278-285.
Garcia-Sastre, A., et al., "Introduction of Foreign Sequences into the Genome of Influenza A Virus", Dev. Biol. Stand. vol. 82, (1994), 237-246.
Garcia-Sastre, A., et al., "Introduction of foreign sequences into the genome of influenza A virus.", Dev Biol Stand., 82, (1994), 237-246.

Garcia-Sastre, A., et al., "Use of a mammalian internal ribosomal entry site element for expression of a foreign protein by a transfectant influenza virus.", Journal of Virology, 68(10), (1994), 6254-6261.
Hughes, M. T, et al., "Influenza A Viruses Lacking Sialidase Activity Can Undergo Multiple Cycles of Replication in Cell Culture, Eggs, or Mice", Journal of Virology, 74(11), (2000), 5206-212.
Neumann, G., et al., "Reverse genetics of influenza virus.", Virology, 287(2), (Sep. 1, 2001), 243-50.
Victor, Sylvia T., et al., "A Replication-Incompetent PB2-Knockout Influenza A Virus Vaccine Vector", Journal of Virology, 86(8), (2012), 4123-4128.
U.S. Appl. No. 16/694,748, filed Nov. 25, 2019, Influenza Viruses with Mutant PB2 Segment as Live Attenuated Vaccines.
"2018-19 ACIP Background—Immunogenicity, Efficacy, and Effectiveness of Influenza Vaccines", [online], [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.
"U.S. Appl. No. 10/081,170, Advisory Action dated Sep. 27, 2004", 3 pgs.
"U.S. Appl. No. 10/081,170, Final Office Action dated Apr. 12, 2006", 7 pgs.
"U.S. Appl. No. 10/081,170, Final Office Action dated Jul. 13, 2004", 8 pgs.
"U.S. Appl. No. 10/081,170, Non Final Office Action dated Jan. 15, 2004", 9 pgs.
"U.S. Appl. No. 10/081,170, Non Final Office Action dated Feb. 8, 2005", 9 pgs.
"U.S. Appl. No. 10/081,170, Non Final Office Action dated Aug. 24, 2005", 9 pgs.
"U.S. Appl. No. 10/081,170, Notice of Allowance dated Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action dated Aug. 24, 2005", 11 pgs.
"U.S. Appl. No. 10/081,170, Response filed Apr. 12, 2004 to Non Final Office Action dated Jan. 15, 2004", 12 pgs.
"U.S. Appl. No. 10/081,170, Response filed Jun. 8, 2005 to Non Final Office Action dated Feb. 8, 2005", 11 pgs.
"U.S. Appl. No. 10/081,170. Response filed Aug. 17, 2006 to Final Office Action dated Apr. 12, 2006", 9 pgs.
"U.S. Appl. No. 10/081,170, Response filed Sep. 13, 2004 to Final Office Action dated Jul. 13, 2004", 10 pgs.
"U.S. Appl. No. 10/081,170, Response filed Oct. 10, 2003 to Restriction Requirement dated Sep. 10, 2003", 3 pgs.
"U.S. Appl. No. 10/081,170, Restriction Requirement dated Sep. 10, 2003", 4 pgs.
"U.S. Appl. No. 11/509,249, Final Office Action dated Jun. 12, 2008", 5 pgs.
"U.S. Appl. No. 11/509,249, Non Final Office Action with Restriction Requirement dated Aug. 24, 2007", 8 pgs.
"U.S. Appl. No. 11/509,249, Notice of Allowance dated Apr. 9, 2009", 7 pgs.
"U.S. Appl. No. 11/509,249, Notice of Allowance dated Nov. 17, 2008", 4 pgs.
"U.S. Appl. No. 11/509,249, Response filed Feb. 20, 2008 to Non Final Office Action dated Aug. 24, 2007", 11 pgs.
"U.S. Appl. No. 11/509,249, Response filed Oct. 6, 2008 to Office Action dated Jun. 12, 2008", 11 pgs.
"U.S. Appl. No. 11/644,179 , Response filed Oct. 21, 2013 to Final Office Action dated May 21, 2013", 8 pgs.
"U.S. Appl. No. 11/644,179, Final Office Action dated May 21, 2013", 11 pgs.
"U.S. Appl. No. 11/644,179, Final Office Action dated Jul. 2, 2010", 8 pgs.
"U.S. Appl. No. 11/644,179, Non Final Office Action dated Nov. 29, 2012", 19 pgs.

(56) References Cited

OTHER PUBLICATIONS

"U.S. Appl. No. 11/644,179, Non Final Office Action dated Dec. 8, 2009", 7 pgs.
"U.S. Appl. No. 11/644,179, Notice of Allowance dated Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement dated Oct. 30, 2007", 5 pgs.
"U.S. Appl. No. 11/644,179, Response filed Apr. 8, 2010 to Non Final Office Action dated Dec. 8, 2009", 8 pgs.
"U.S. Appl. No. 11/644,179, Response filed Aug. 17, 2010 to Final Office Action dated Jul. 2, 2010", 8 pgs.
"U.S. Appl. No. 11/644,179, Restriction Requirement dated Oct. 30, 2007", 7 pgs.
"U.S. Appl. No. 11/644,179, Supplemental Preliminary Amendment filed Feb. 6, 2008", 6 pgs.
"U.S. Appl. No. 11/644,179. Response filed Feb. 20, 2013 to Non Final Office Action dated Nov. 29, 2012", 10 pgs.
"U.S. Appl. No. 12/113,690, Final Office Action dated Apr. 15, 2011", 10 pgs.
"U.S. Appl. No. 12/113,690, Non-Final Office Action dated Nov. 10, 2010", 11 pgs.
"U.S. Appl. No. 12/113,690, Notice of Allowability dated Aug. 19, 2013", 9 pgs.
"U.S. Appl. No. 12/113,690, Notice of Allowance dated Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action dated Apr. 15, 2011", 17 pgs.
"U.S. Appl. No. 12/113,690, Response filed Aug. 5, 2010 to Restriction Requirement dated Apr. 6, 2010", 14 pgs.
"U.S. Appl. No. 12/113,690, Response filed Dec. 22, 2010 to Non Final Office Action dated Nov. 10, 2010", 19 pgs.
"U.S. Appl. No. 12/113,690, Restriction Requirement dated Apr. 6, 2010", 10 pgs.
"U.S. Appl. No. 12/470,287 , Response filed Jan. 23, 2012 to Non Final Office Action dated Jul. 22, 2011", 13 pgs.
"U.S. Appl. No. 12/470,287 , Response filed May 31, 2012 to Final Office Action dated Apr. 3, 2012", 14 pgs.
"U.S. Appl. No. 12/470,287, Corrected Notice of Allowability dated Sep. 11, 2012", 2 pgs.
"U.S. Appl. No. 12/470,287, Final Office Action dated Apr. 3, 2012", 7 pgs.
"U.S. Appl. No. 12/470,287, Non Final Office Action dated Jul. 22, 2011", 9 pgs.
"U.S. Appl. No. 12/470,287, Notice of Allowance dated Jun. 19, 2012", 5 pgs.
"U.S. Appl. No. 12/470,287, Response filed Apr. 28, 2011 to Restriction Requirement dated Dec. 29, 2010", 8 pgs.
"U.S. Appl. No. 12/470,287, Restriction Requirement dated Dec. 29, 2010", 6 pgs.
"U.S. Appl. No. 13/594,611, Final Office Action dated Aug. 15, 2014", 7 pgs.
"U.S. Appl. No. 13/594,611, Non Final Office Action dated Apr. 24, 2014", 9 pgs.
"U.S. Appl. No. 13/594,611, Notice of Allowance dated Jan. 13, 2015", 7 pgs.
"U.S. Appl. No. 13/594,611, PTO Response to Rule 312 Communication dated Apr. 16, 2015", 2 pgs.
"U.S. Appl. No. 13/594,611, Response filed Feb. 25, 2014 to Restriction Requirement dated Jan. 27, 2014", 8 pgs.
"U.S. Appl. No. 13/594,611, Response filed Jul. 7, 2014 to Non Final Office Action dated Apr. 24, 2014", 9 pgs.
"U.S. Appl. No. 13/594,611, Response filed Dec. 15, 2014 to Final Office Action dated Aug. 15, 2014", 10 pgs.
"U.S. Appl. No. 13/594,611, Restriction Requirement dated Jan. 27, 2014", 8 pgs.
"U.S. Appl. No. 14/699,213, Advisory Action dated Mar. 7, 2018", 3 pgs.
"U.S. Appl. No. 14/699,213, Final Office Action dated Dec. 1, 2017", 11 pgs.
"U.S. Appl. No. 14/699,213, Non Final Office Action dated Jun. 2, 2017", 12 pgs.
"U.S. Appl. No. 14/699,213, Non-Final Office Action dated Jan. 11, 2019", 10 pgs.
"U.S. Appl. No. 14/699,213, Preliminary Amendment filed Apr. 30, 2015", 8 pgs.
"U.S. Appl. No. 14/699,213, Response filed Feb. 15, 2017 to Restriction Requirement dated Aug. 15, 2016", 9 pgs.
"U.S. Appl. No. 14/699,213, Response filed Feb. 27, 2018 to Final Office Action dated Dec. 1, 2017", 34 pgs.
"U.S. Appl. No. 14/699,213, Response filed Aug. 22, 2011 to Non Final Office Action dated Jun. 2, 2017", 12 pgs.
"U.S. Appl. No. 14/699,213, Restriction Requirement dated Aug. 15, 2016", 10 pgs.
"U.S. Appl. No. 15/247,006 Response filed Jun. 4, 2019 to Final Office Action dated Feb. 4, 2019", 7 pgs.
"U.S. Appl. No. 15/247,006, Examiner Interview Summary dated Nov. 27, 2017", 4 pgs.
"U.S. Appl. No. 15/247,006, Final Office Action dated Feb. 4, 2019", 8 pgs.
"U.S. Appl. No. 15/247,006, Non Final Office Action dated Apr. 20, 2018", 7 pgs.
"U.S. Appl. No. 15/247,006, Non Final Office Action dated Sep. 8, 2017", 8 pgs.
"U.S. Appl. No. 15/247,006, Notice of Allowance dated Jun. 24, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement dated Mar. 17, 2017", 12 pgs.
"U.S. Appl. No. 15/247,006, Response filed Oct. 22, 2018 to Non Final Office Action dated Apr. 20, 2018", 14 pgs.
"U.S. Appl. No. 15/247,006, Response filed Dec. 7, 2017 to Non Final Office Action dated Sep. 8, 2017", 13 pgs.
"U.S. Appl. No. 15/247,006, Restriction Requirement dated Mar. 17, 2017", 9 pgs.
"Australian Application Serial No. 2003219745, Examiner's First Report dated Feb. 14, 2007", 2 pgs.
"Australian Application Serial No. 2003219745, Response filed Mar. 14, 2008 to Examiner's First Report dated Feb. 14, 2007", 24 pgs.
"Australian Application Serial No. 2008203186, First Examiner Report dated Jan. 28, 2011", 2 pgs.
"Australian Application Serial No. 2008203186, Office Action Received dated Sep. 16, 2010", 1 page.
"Australian Application Serial No. 2008203186, Response filed Mar. 28, 2011 to First Examiner Report dated Jan. 28, 2011", 51 pgs.
"Australian Application Serial No. 2008203186, Response filed Aug. 29, 2011 to Official Action dated Apr. 13, 2011", 20 pgs.
"Australian Application Serial No. 2008203186, Subsequent Examiner Report dated Apr. 13, 2011", 2 pgs.
"Brazil Application Serial No. PI0307679-2, Office Action dated May 16, 2017", 2 pgs.
"Brazil Application Serial No. PI0307679-2, Response filed Jul. 13, 2017 to Office Action dated May 16, 2017", 9 pgs.
"Canadian Application Serial No. 11/509,249, Response filed May 16, 2011 to Office Acttion dated Nov. 18, 2010", 15 pgs.
"Canadian Application Serial No. 2,492,097, Office Action dated Jan. 10, 2012", 4 pgs.
"Canadian Application Serial No. 2,492,097, Office Action dated Apr. 24, 2008", 3 pgs.
"Canadian Application Serial No. 2,492,097, Office Action dated Jul. 31, 2009", 3 pgs.
"Canadian Application Serial No. 2,492,097, Response filed Jan. 29, 2010 to Office Action dated Jul. 31, 2009", 13 pgs.
"Canadian Application Serial No. 2,492,097, Response filed May 2, 2012 to Office Action dated Jan. 10, 2012", 12 pgs.
"Canadian Application Serial No. 2,492,097, Response filed Oct. 23, 2008 to Office Action dated Apr. 24, 2008", 14 pgs.

(56) References Cited

OTHER PUBLICATIONS

"Canadian Application Serial No. 2,816,242, Office Action dated Jun. 16, 2014", 3 pgs.
"Canadian Application Serial No. 2,816,242, Office Action dated Jul. 12, 2017", 4 pgs.
"Canadian Application Serial No. 2,816,242, Office Action dated Sep. 16, 2016", 4 pgs.
"Canadian Application Serial No. 2,816,242, Office Action dated Oct. 5, 2015", 6 pgs.
"Canadian Application Serial No. 2,816,242, Response filed Jan. 3, 2018 to Office Action dated Jul. 12, 2017", 13 pgs.
"Canadian Application Serial No. 2,816,242, Response filed Mar. 10, 2017 to Office Action dated Sep. 16, 2016", 18 pgs.
"Canadian Application Serial No. 2,816,242, Response filed Apr. 5, 2016 to Office Action dated Oct. 5, 2015", 13 pgs.
"Canadian Application Serial No. 2,816,242, Response filed Dec. 16, 2014 to Office Action dated Jun. 16, 2014", 9 pgs.
"Canadian Application Serial No. 2492097, Office Action dated Nov. 18, 2010", 4 pgs.
"Chinese Application Serial No. 03808356.6, Office Action dated Sep. 5, 2008", (English Translation), 6 pgs.
"Chinese Application Serial No. 03808356.6, Office Action dated Jul. 1, 2011", (w/ English Translation of Office Action), 8 pgs.
"Chinese Application Serial No. 03808356.6, Reexamination Notice dated Nov. 26, 2012", (w/English Translation), 9 pgs.
"Chinese Application Serial No. 03808356.6, Response filed Mar. 11, 2013 to Office Action dated Nov. 26, 2012", (w/ English Translation of Amended Claims), 9 pgs.
"Chinese Application Serial No. 03808356.6, Response filed Mar. 16, 2009 to Office Action dated Sep. 5, 2008", (w/ English Translation of Claims), 8 pgs.
"Chinese Application Serial No. 03808356.6, Response filed Oct. 14, 2011 to Office Action dated Jul. 1, 2011", (w/ English Translation of Amended Claims), 25 pgs.
"Chinese Application Serial No. 201310400039.8, Notice of Reexamination dated Aug. 26, 2016", (w/ English Translation), 7 pgs.
"Chinese Application Serial No. 201310400039.8, Office Action dated Feb. 12, 2015", (w/ English Translation), 10 pgs.
"Chinese Application Serial No. 201310400039.8, Office Action dated Feb. 15, 2016", (w/ English Translation), 12 pgs.
"Chinese Application Serial No. 201310400039.8, Office Action dated Apr. 1, 2017", (English Translation), 10 pgs.
"Chinese Application Serial No. 201310400039.8, Office Action dated Aug. 7, 2015", (w/ English Translation), 10 pgs.
"Chinese Application Serial No. 201310400039.8, Office Action dated Aug. 21, 2014", (w/ English Translation), 13 pgs.
"Chinese Application Serial No. 201310400039.8, Office Action Response dated Jun. 16, 2017", W / English Claims, 8 pgs.
"Chinese Application Serial No. 201310400039.8, Response filed Jan. 4, 2015 to Office Action dated Aug. 21, 2014", (w/ English Translation of Claims), 10 pgs.
"Chinese Application Serial No. 201310400039.8, Response filed Apr. 27, 2015 to Office Action dated Feb. 12, 2015", (w/ English Translation of Claims), 16 pgs.
"Chinese Application Serial No. 201310400039.8, Response filed Jun. 1, 2016 to Office Action dated Feb. 15, 2016", (w/ English Translation of Claims), 9 pgs.
"Chinese Application Serial No. 201310400039.8, Response filed Oct. 10, 2016 to Notice of Reexamination dated Aug. 26, 2016", (w/ English Translation of Claims), 12 pgs.
"Chinese Application Serial No. 201310400039.8, Response filed Oct. 20, 2015 to Office Action dated Aug. 7, 2015", (w/ English Translation of Claims), 11 pgs.
"Chinese Application Serial No. 201310400039.8, Response filed Aug. 14, 2017 to Office Action Response dated Jun. 16, 2017", W/ English Claims.
"Chinese Application Serial No. 201310400039.8, Response filed Aug. 7, 2017 to Office Action Response dated Jun. 16, 2017", W/ English Claims, 10 pgs.

"European Application Serial No. 03716017.3, Office Action dated Aug. 23, 2012", 4 pgs.
"European Application Serial No. 02724994.5, Office Action dated Mar. 27, 2009", 2 pgs.
"European Application Serial No. 03716017.3, Communication and Supplementary European Search Report dated Jan. 2, 2008", 8 pgs.
"European Application Serial No. 03716017,3, Communication dated May 23, 2006", 3 pgs.
"European Application Serial No. 03716017.3, Communication dated Jul. 26, 2006", 2 pgs.
"European Application Serial No. 03716017.3, Communication dated Oct. 20, 2008", 7 pgs.
"European Application Serial No. 03716017.3, Further Written Submissions filed Mar. 19, 2015", 45 pgs.
"European Application Serial No. 03716017.3, Office Action dated Jul. 27, 2010", 4 pgs.
"European Application Serial No. 03716017.3, Response filed Feb. 4, 2011 to Office Action dated Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) dated Aug. 23, 2012", 19 pgs.
"European Application Serial No. 03716017.3, Response filed Mar. 24, 2015 to Office Action dated Nov. 3, 2014", 38 pgs.
"European Application Serial No. 03716017.3, Response filed Jul. 28, 2006 to Communication dated May 23, 2006", 5 pgs.
"European Application Serial No. 03716017.3, Response filed Aug. 19, 2009 to Communication dated Oct. 20, 2008", 17 pgs.
"European Application Serial No. 03716017.3, Response filed Sep. 28, 2015", 15 pgs.
"European Application Serial No. 03716017.3, Result of Consultation dated Mar. 17, 2015", 5 pgs.
"European Application Serial No. 03716017.3, Summons to Attend Oral proceedings dated Nov. 3, 2014", 5 pgs.
"European Application Serial No. 12761841.1, Communication pursuant to Article 94(3) EPC dated Dec. 23, 2016", 6 pgs.
"European Application Serial No. 12761841.1, Response filed Feb. 23, 2017 to Communication pursuant to Article 94(3) EPC dated Dec. 23, 2016", 9 pgs.
"European Application Serial No. 12761841.1, Voluntary Amendment filed Dec. 1, 2014", 5 pgs.
"European Application Serial No. 15197386.4, Communication Pursuant to Article 94(3) EPC dated Feb. 21, 2018", 5 pgs.
"European Application Serial No. 15197386.4, Communication Pursuant to Article 94(3) EPC dated Apr. 21, 2017", 5 pgs.
"European Application Serial No. 15197386.4, extended European Search Report dated Feb. 26, 2016", 11 pgs.
"European Application Serial No. 15197386.4, Response filed Jul. 3, 2018 to Communication Pursuant to Article 94(3) EPC dated Feb. 21, 2018", 7 pgs.
"European Application Serial No. 15197386.4, Response filed Oct. 20, 2016 to Extended European Search Report dated Feb. 26, 2016", 4 pgs.
"European Application Serial No. 15197386.4, Response filed Oct. 31, 2017 to Communication Pursuant to Article 94(3) EPC dated Apr. 21, 2017", 5 pgs.
"European Application Serial No. 16778485.9, Office Action dated Apr. 30, 2018", 3 pgs.
"European Application Serial No. 16778485.9, Response filed Nov. 8, 2018 to Office Action dated Apr. 30, 2018", 18 pgs.
"Influenza virus A/CHR/ 157/83 genomic RNA for haemagglutinin", 2 pgs.
"International Application Serial No. PCT/US02/05455, International Preliminary Examination Report dated Aug. 17, 2004", 4 pgs.
"International Application Serial No. PCT/US02/05455, International Search Report dated Mar. 25, 2003", 3 pgs.
"International Application Serial No. PCT/US03/04233, International Search Report dated Dec. 16, 2005", 7 pgs.
"International Application Serial No. PCT/US2003/004233, International Search Report dated Dec. 16, 2005", 5 pgs.

(56) References Cited

OTHER PUBLICATIONS

"International Application Serial No. PCT/US2008/005641, International Preliminary Report on Patentability dated Nov. 10, 2009", 9 pgs.
"International Application Serial No. PCT/US2008/005641, International Search Report dated Feb. 4, 2009", 6 pgs.
"International Application Serial No. PCT/US2008/005641, Written Opinion dated Feb. 4, 2009", 8 pgs.
"International Application Serial No. PCT/US2012/052368, International Preliminary Report on Patentability dated Mar. 13, 2014", 8 pgs.
"International Application Serial No. PCT/US2012/052368, International Search Report dated Dec. 3, 2012", 4 pgs.
"International Application Serial No. PCT/US2012/052368, Written Opinion dated Dec. 3, 2012", 6 pgs.
"International Application Serial No. PCT/US2016/048691, International Preliminary Report on Patentability dated Mar. 15, 2018", 7 pgs.
"International Application Serial No. PCT/US2016/048691, International Search Report dated Nov. 22, 2016", 7 pgs.
"International Application Serial No. PCT/US2016/048691, Written Opinion dated Nov. 22, 2016", 6 pgs.
"Israel Application Serial No. 163,546, First Examination Report dated Jul. 28, 2008", (English Translation), 2 pgs.
"Israel Application Serial No. 163,546, Office Action dated Nov. 12, 2009", (English Translation), 1 pg.
"Israel Application Serial No. 163,546, Office Action dated Dec. 26, 2007", (English Translation), 1 pg.
"Israel Application Serial No. 163,546, Response filed May 9, 2008 to Office Action dated Dec. 26, 2007", (English Translation of Amendments), 2 pgs.
"Israel Application Serial No. 163,546, Response filed Jun. 8, 2010 to Office Action dated Nov. 12, 2009", (English Translation of Claims), 3 pgs.
"Israel Application Serial No. 163,546, Response filed Aug. 16, 2009 to Substantive Examination Report dated Feb. 23, 2009", (English Translation of Claims), 4 pgs.
"Israel Application Serial No. 163,546, Response filed Oct. 20, 2010 to Office Action dated Jun. 8, 2010", (w/ Rnglish Translation of Claims), 8 pgs.
"Israel Application Serial No. 163,546, Response filed Nov. 27, 2008 to First Examination Report dated Jul. 28, 2008", (w English Translation of Claims), 13 pgs.
"Israel Application Serial No. 163546, Office Action dated Jun. 8, 2010", (w/ English Translation), 2 pgs.
"Israeli Application Serial No. 163,546, First Examination Report dated Jul. 28, 2008", (English Translation), 2 pgs.
"Israeli Application Serial No. 163,546, Substantive Examination Report dated Feb. 23, 2009", (English Translation), 3 pgs.
"Israeli Application Serial No. 211324, Office Action dated Sep. 18, 2014", (English Translation), 5 pgs.
"Israeli Application Serial No. 211324, Office Action dated Oct. 18, 2015", (w/ English Translation), 4 pgs.
"Israeli Application Serial No. 211324, Response filed Feb. 16, 2016 to Office Action dated Oct. 18, 2015", (English Translation of Claims) , 4 pgs.
"Israeli Application Serial No. 211324, Response filed Mar. 31, 2015 to Office Action dated Sep. 8, 2014", (w/ English Translation), 21 pgs.
"Japanese Application Serial No. 2003-315106, Amended Claims filed Oct. 15, 2009 in Response to Office Action dated Jun. 24, 2009", (English Translation), 6 pgs.
"Japanese Application Serial No. 2003-315106, Office Action dated Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Office Action dated May 15, 2009", (w/ English Translation), 7 pgs.
"Japanese Application Serial No. 2003-568038, Office Action dated Jul. 10, 2008", (w/ English Translation), 11 pgs.
"Japanese Application Serial No. 2003-568038, Office Action dated Jul. 21, 2005", 3 pgs.
"Japanese Application Serial No. 2003-568038, Request for Examination filed Aug. 19, 2005 in Response to Official Action dated Jul. 21, 2005", (w/ Partial English Translation of Specification), 8 pgs.
"Japanese Application Serial No. 2003-568038, Response filed Sep. 14, 2009 to Office Action dated May 15, 2009", (w/ English Translation of Amended Claims), 10 pgs.
"Japanese Application Serial No. 2003-568038, Response filed Dec. 10, 2008 to Office Action dated Jul. 10, 2008", (w/ English Translation of Amended Claims), 15 pgs.
"Japanese Application Serial No. 2008-315106, Office Action dated Jun. 24, 2009", (w/ English Translation), 10 pgs.
"Japanese Application Serial No. 2008-315106, Response filed Oct. 15, 2009 to Office Action dated Jun. 24, 2009", 103 pgs.
"Japanese Application Serial No. 2008-315106, Response filed Oct. 15, 2009 to Office Action dated Jun. 24, 2009", (w/ English Translation of Amended Claims), 103 pgs.
"Japanese Application Serial No. 2008-315106, Response filed Dec. 3, 2009 to Office Action dated Jun. 24, 2009", (w/ English Translation of Claims), 9 pgs.
"Japanese Application Serial No. 2009-238781, Office Action dated Oct. 11, 2011", (w/ English Translation), 3 pgs.
"Japanese Application Serial No. 2014-527339, Examiners Decision of Final Refusal dated Feb. 7, 2017", (w/ English Translation), 5 pgs.
"Japanese Application Serial No. 2014-527339, Office Action dated May 31, 2016", (w/ English Translation), 10 pgs.
"Japanese Application Serial No. 2014-527339, Response filed Sep. 16, 2016 to Office Action dated May 31, 2016", (w/ English Translation of Amended Claims), 33 pgs.
"Japanese Application Serial No. 2017-111526, Office Action dated Jun. 26, 2018", (w/ English Translation), 5 pgs.
"Japanese Application Serial No. 2017-111526, Response Filed Dec. 21, 2018 to Office Action dated Jun. 26, 2018", (w/ English Translation of Amended Claims), 7 pgs.
"Korean Application Serial No. 10-2004-7012647, Office Action dated Feb. 26, 2010", (w/ English Translation), 7 pgs.
"Korean Application Serial No. 10-2004-7012647, Response filed Jun. 10, 2010 to Office Action dated Feb. 26, 2010", (w/ English Translation of Claims), 17 pgs.
"Korean Application Serial No. 10-2010-7011520, Office Action dated Jul. 20, 10", (w/ English Translation), 6 pgs.
"Korean Application Serial No. 10-2010-7011520, Response filed Oct. 20, 2010 to Office Actiion dated Jul. 20, 2010", (w/ English Translation of Amended Claims), 30 pgs.
"Korean Application Serial No. 10-2010-7011520, Amended Claims filed May 24, 2011 in Response to Office Action dated Feb. 24, 2011", (English Translation of Amended Claims), 22 pgs.
"Korean Application Serial No. 10-2010-7011520, Office Action dated Feb. 24, 2011", (w/ English Translation), 5 pgs.
"Mexican Application Serial No. PA/a/2004/007914, Office Action dated Feb. 14, 2008", (w/ English Translation), 3 pgs.
"Mexican Application Serial No. PA/a/2004/007914, Office Action dated Feb. 22, 2008", (English Translation), 3 pgs.
"Mexican Application Serial No. PA/a/2004/007914, Response filed Jun. 11, 2008 to Office Action dated Feb. 22, 2008", (w/ English Translation of Claims), 68 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structrure of Small Viral RNA Segment", Database UniProt EBI / Accession No. NC_002023, (Jul. 10, 2008), 15 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Castrucci, M. R, et al., "Attenuation of Influenza A Virus by Insertion of a Foreign Epitope into the Neuraminidase", Journal of Virology, 66(8), (1992), 4647-4653.

(56) References Cited

OTHER PUBLICATIONS

Castrucci, M. R., et al., "Biologic Importance of Neuraminidase Stalk Length in Influenza A Virus", Journal of Virology, 67(2), (1993), 759-764.

Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.

Catchpole, A P, et al., "Alternative base pairs attenuate influenza A virus when introduced into the duplex region of the conserved viral RNA promoter of either the NS or the PA gene", Journal of General Virology, 84, (2003), 507-515.

Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.

Del Guidice, G., et al., "What are the limits of adjuvanticity?", (Abstract), Vaccine, 20(Suppl 1), S38-S41, (2001), 1 pg.

Desselberger, Ulrich, et al., "The 3' and 5'-terminal sequences of influenza A, B and C virus RNA segments are highly conserved and show partial inverted complementarity", Gene, 8 (3), (Feb. 1980), 315-328.

Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.

Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.

Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, Us, (Sep. 1, 1998), 241-253.

Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.

Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy". Journal of Virology. 74(15). (Aug. 2000), 6821-6831.

Essere, Boris, et al., "Critical role of segment-specific packaging signals in genetic reassortment of influenza A viruses", Proc. Natl. Acad. Sci. USA, 110(40), (2013), E3840-E3848.

Fields, S., et al., "Nucleotides Sequences of Influenza Virus Segments 1 and 3 Reveal Mosaic Structrure of Small Viral RNA Segment", Cell, 28, (1982), 303-313.

Flandorfer, A., et al., "Chimeric Influenza A Viruses with a Functional Influenza B Virus Neuraminidase or Hemagglutinin", Journal of Virology, 77(17), (2003), 9116-9123.

Fuji, Y., et al., "Selective incorporation of influenza virus RNA segments into virions", Proc. Natl. Acad. Sci. USA, 100(4), (2003), 2002-2007.

Fujii, Y, et al., "The packaging of influenza viral genome", Virus, 52 (1), Uirusu (Japanese Journal Name), (Jun. 2002), 203-206.

Gao, Qinshan, et al., "A Seven-Segmented Influenza A Virus Expressing the Influenza C Virus Glycoprotein HEF", Journal of Virology, 82(13), (Jul. 2008), 6419-6426.

Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.

Garcia-Sastre, Adolfo, et al., "Use of a Mammalian Internal Ribosomal Entry Site Element for Expression of a Foreign Protein by a Transfectant Influenza Virus", Journal of Virology, 68(10), (Jun. 30, 1994), 6254-6261.

Ghate, Anita A, et al., "Influenza Type B Neuraminidase Can Replace the Function of Type A Neuraminidase", Virology, 264 (2), (Nov. 1999), 265-277.

Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.

Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.

Green, R. F., et al., "Glycosylation Does Not Determine Segregation of Viral Envelope Proteins in the Plasma Membrane of Epithelial Ceils", J. Cell Biol., 89(2), (1981), 230-239.

Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.

Hiti, A. L., et al., "P03470—Neuraminidase", Entrez Protein Database, http://www.ncbi.nlm.nih.gov/entrez/viewer.fcgi?db=protein &val=84028231, (1982), 730-734.

Hiti, A. L., et al., "P03470—Neuraminidase", Entrez Protein Database, [online], [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).

Hossain, M. J., et al., "Establishment and Characterization of a Madin-Darby Canine Kidney Reporter Cell Line for Influenza A Virus Assays", J Clin Microbiol, 48(7), (2010), 2515-2523.

Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.

Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.

Hutchinson, Edward C., et al., "Genome packaging in influenza A virus", Journal of General Virology, 91(Pt 2), (2010), 313-328.

Hwang, Jung-Shan, et al., "Expression of Functional Influenza Virus RNA Polymerase in the Methylotrophic Yeast *Pichia pastoris*", Journal of Virology, 74(9), (2000), 4074-4084.

Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.

Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.

Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.

Kobayashi, H., et al., "A replication-incompetent influenza virus bearing the HN glycoprotein of human parainfluenza virus as a bivalent vaccine". Vaccine, 31(52), (2013), 6239-6246.

Latham, T, et al., "Formation of Wild-Type and Chimeric Influenza Virus-Like Particles following Simultaneous Expression of Only Four Structural Proteins", Journal of Virology 75 (13), (2001), 6154-6165.

Leal, et al., "New challenges in therapeutic vaccines against HIV infection", Expert Review of Vaccines, vol. 16, No. 6, (2017), 587-600.

Lee, D.-H., et al., "H9N2 avian influenza virus-like particle vaccine provides protective immunity and a strategy for the differentiation of infected from vaccinated animals", Vaccine, vol. 29, (2011), 4003-4007.

Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.

(56) References Cited

OTHER PUBLICATIONS

Li, S., et al., "Influenza A Virus Transfectants with Chimeric Hemagglutinins Containing Epitopes from Different Subtypes", Journal of Virology, 66(1), (1992), 399-404.

Li, S., et al., "Recombinant Influenza A Virus Vaccines for the Pathogenic Human A/Hong Kong/97 (H5N1) Viruses", J Infect Dis., 179(5), (1999), 1132-1138.

Liu, C., et al., "Influenza type A virus neuraminidase does not play a role in viral entry, replication, assembly, or budding.", Journal of Virology, 69(2), (1995), 1099-1106.

Liu, C., et al., "Selection and Characterization of a Neuraminidase-Minus Mutant of Influenza Virus and its Rescue by Cloned Neuraminidase Genes", Virology, 194(1), (1993), 403-407.

Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.

Luytjes, W., "Amplification, Expression, and Packaging of a Foreign Gene by Influenza Virus", Cell, 59(6), (1989), 1107-1113.

Manicassamy, Balaji, et al., "Analysis of in vivo dynamics of influenza virus infection in mice using a GFP reporter virus", Proc Natl Acad Sci. USA, 107(25), (2010), 11531-11536.

Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.

Martin, J., et al., "Studies of the Binding Properties of Influenza Hemagglutinin Receptor-Site Mutants", Virology, 241(1), (Feb. 1, 1998), 101-111.

Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.

Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.

Matta, M, et al., "Cell-surface sialoglycoconjugate structures in wild-type and mutant Crithidia fasciculata", Parasitol. Res., 85(4), (1999), 293-299.

Mishin, V. P, et al., "Protection afforded by intranasal immunization with the neuraminidase-lacking mutant of influenza A virus in a ferret model", Vaccine, 23(22), (Apr. 22, 2005), 2922-7.

Mitnaul, L. J., et al., "Balanced Hemagglutinin and Neuraminidase Activities are Critical for Efficient Replication of Influenza A Virus", Journal of Virology, 74 (13), (2000), 6015-6020.

Muramoto, Y., et al., "Hierarchy among Viral RNA (vRNA) Segments in Their Role in vRNA Incorporation into Influenza A Virions", J. Virol., 80(5), (2006), 2318-2325.

Muramoto, Yukiko, "Hierarchy among Viral RNA (vRNA) Segments in Their Role in vRNA Incorporation into Influenza A Virions", Journal of Virology, 80(5), (2006), 2318-2325.

Murphy, B. R, et al., "An influenza A live attenuated reassortant virus possessing three temperature-sensitive mutations in the PB2 polymerase gene rapidly loses temperature sensitivity following replication in hamsters", Vaccine,15(12-13), (Aug-Sep. 1997), 1372-8.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Neumann, G., et al., "Generation of influenza A viruses entirely from cloned cDNAs". Proc. Natl. Acad. Sci. USA., 96(16), (1999), 9345-9350.

Neumann, G., et al., "Influenza A virus NS2 protein mediates vRNP nuclear export through NES-independent interaction with hCRM1", The EMBO Journal, 19 (24), (2000), 6751-6758.

Neumann, G., et al., "Mutational analysis of influenza virus promoter elements in vivo", Journal of General Virology, 76, (1995), 1709-1717.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "Reverse Genetics of Influenza Viruses—Applications in Research and Vaccine Design", Monographs in Virology, 27, (2008), 118-133.

Neumann, Gabriele, "Minireview Reverse Genetics of Influenza Virus", Virology, vol. 287, (2001), 243-250.

Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3). (1997), 2138-2145.

Ozawa, M., et al., "Replication-incompetent influenza A viruses that stably express a foreign gene", Journal of General Virology, 92(Part 12)., (2011), 2879-2888.

Pattnaik, A. K., et al., "The Termini of VSV DI Particle RNAs are Sufficient to Signal RNA Encapsidation. Replication, and Budding to Generate Infectious Particles", Virology, 206, (1995), 760-764.

Percy, N., et al., "Expression of a Foreign Protein by Influenza A Virus", Journal of Virology, 68(7), (1994), 4486-4492.

Piatti, G., "Identification of immunodominant epitopes In the filamentous Hemagglutinin of Bordetella pertusis", FEMS Immunology and Medical Microbiology, 23(3), (1999), 235-241.

Portela, A., et al., "Replication of orthomyxoviruses", Advances in Virus Research, 54, (1999), 319-348.

Ray, M. K., et al., "A Novel Glycosylation Phenotype Expressed by Lec23, a Chinese Hamster Ovary Mutant Deficient in alpha-Glucosidase I", Journal of Biological Chemistry. 266(34), (1991), 22818-22825.

Rayner, J., et al., "Alphavirus vectors and vaccination", Reviews in Medical Virology, 12, (2002), 279-296.

Restifo, N. P., et al., "Transfectant Influenza A Viruses are Effective Recombinant Immunogens in the Treatment of Experimental Cancer", Virology, 249(1), (1998), 89-97.

Rimmelzwaan, G. F., et al., "Use of GFP-expressing influenza viruses for the detection of influenza virus A/H5N1 neutralizing antibodies", Vaccine, 29(18), (2011), 3424-3430.

Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.

Schultz-Cherry, S., et al., "Influenza Virus NS1 Protein Induces Apoptosis in Cultured Cells", Journal of Virology, 75(17), (2001), 7875-7881.

Shengqiang, Li, et al., "Influenza A Virus Transfectants with Chimeric Hemagglutinins containing Epitopes from different subtypes", Journal of Virology, (1992), 399-404.

Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.

Stray, S. J., et al., "Influenza virus infection of desialylated cells", Glycobiology, 10(7), (2000), 649-658.

Strobel, I., et al., "Efficient Expression Of The Tumor-Associated Antigen MAGE-3 In Human Dendritic Cells, Using An Avian Influenza Virus Vector", Human Gene Therapy, 11(16), (2000), 2207-2218.

Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.

Terry, G., et al., "The Contruction of Defective Interfering Rubella Virus Particles", Archives of Virology, 145(3), (2000), 625-633.

Thompson, Christine M, et al., "Critical assessment of influenza VLP production in Sf9 and HEK293 expression systems", BMC Biotechnology, 15(1), (May 16, 2015), 12 pgs.

(56) References Cited

OTHER PUBLICATIONS

Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.

Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.

Victor, Sylvia, et al., "A Replication-Incompetent PB2-Knockout Influenza A Virus Vaccine Vector", Journal of Virology, vol. 86, No. 8, (Apr. 2012), 4123-4128.

Walker, W. S, et al., "HEL-Flu: an influenza virus containing the hen egg lysozyme epitope recognized by CD4+ T cells from mice transgenic for an alphabeta TCR". J. Immunol., 159(6), (Sep. 1997), 2563-2566.

Watanabe, S., et al., "Influenza A Virus Lacking M2 Protein as a Live Attenuated Vaccine", Journal of Virology, 83(11), (2009), 5947-5950.

Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.

Yang, P., et al., "Hemagglutinin Specificity and Neuraminidase Coding Capacity of Meuraminidase-Deficient Influenza Viruses", Virology, 229(1), (1997), 155-165.

Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.

Zhao, Lili, et al., "New Insights into the Nonconserved Noncoding Region of the Subtype-Determinant Hemagglutinin and Neuraminidase Segments of Influenza A aViruses", Journal of Virology, 88(19), (Oct. 2014), 11493-11503.

Zhou, Yan, "Membrane-Anchored Incorporation of a Foreign Protein in Recombinant Influenza Virions", Virology 246(1), (1998), 83-94.

U.S. Appl. No. 10/366,630, U.S. Pat. No. 7,226,774, filed Feb. 12, 2003, Signal for Packaging of Influenza Virus Vectors.

U.S. Appl. No. 11/509,249, U.S. Pat. No. 7,585,657, filed Aug. 24, 2006, Signal for Packaging of Influenza Virus Vectors.

U.S. Appl. No. 12/470,287, U.S. Pat. No. 8,298,805, filed May 21, 2009, Signal for Packaging of Influenza Virus Vectors.

U.S. Appl. No. 13/594,611, U.S. Pat. No. 9,101,653, filed Aug. 24, 2012, Influenza Viruses with Mutant PB2 Gene Segment as Live Attenuated Vaccines.

U.S. Appl. No. 14/699,213, filed Apr. 29, 2015, Influenza Viruses with Mutant PB2 Segment as Live Attenuated Vaccines.

U.S. Appl. No. 15/247,006, filed Aug. 25, 2016, Generation of Infectious Influenza Viruses From Virus-Like Particles.

"U.S. Appl. No. 16/694,748, Restriction Requirement dated Jan. 27, 2021", 9 pgs.

"Japanese Application Serial No. 2020-073952, Notification of Reasons for Refusal dated May 20, 2021", w/o English Translation, 2 pgs.

GENERATION OF INFECTIOUS INFLUENZA VIRUSES FROM VIRUS-LIKE PARTICLES

CROSS-REFERENCE TO RELATED APPLICATIONS

This application is a divisional of U.S. application Ser. No. 15/247,006, filed Aug. 25, 2016, which claims the benefit of the filing date of U.S. application Ser. No. 62/211,125, filed on Aug. 28, 2015, the disclosures of which are incorporated by reference herein.

STATEMENT OF GOVERNMENT RIGHTS

This invention was made with government support under HHSN272201400008C awarded by the National Institutes of Health. The government has certain rights in the invention.

BACKGROUND

Influenza A, B, and C viruses are members of the *Othomyxoviridae*, which is a family of enveloped viruses with segmented, single-stranded, negative-sense RNA genomes. They are classified by antigenic differences in their nucleo-protein (NP) and matrix protein (M1), which are present within the virions. Influenza A viruses are further classified into 18 hemagglutinin (HA) subtypes (H1-H18) and 11 neuraminidase (NA) subtypes (N1-N11) on the basis of the antigenicities of their HA and NA. Most subtypes can be found in their natural reservoir of wild aquatic birds, but they can also infect mammalian species, such as humans, pigs, and horses. Influenza A viruses cause annual epidemics in humans and occasional pandemics that spread on a global scale with severe consequences for human health. Influenza B viruses naturally infect humans, and occasionally seals, and cause more limited epidemics than Influenza A viruses in humans every few years. Influenza C viruses infect humans and pigs. Seroepidemiological studies suggest that influenza C virus has been globally distributed, although it is clinically benign in humans.

Influenza A virions possess a lipid envelope that is acquired from the apical plasma membrane of infected cells during the budding process. The virions released from infected cells are generally spherical, ranging from approximately 80-120 nm in diameter. On the other hand, budding virions on the surface of infected cells present as mostly elongated particles and occasionally filamentous particles of uniform diameter. These virions are covered with projections called spikes. A large number of two glycoproteins, HA and NA, and small amounts of an ion channel protein (M2) are inserted into the envelope. The two glycoproteins form the spikes on the viral surface. The HA spikes are rod-shaped, while the NA spikes are mushroom-shaped with a box-shaped head that is connected to the lipid membrane by a stalk. M1, a peripheral membrane protein, is one of the most abundant viral proteins in the virion. It binds to the lipid envelope and is thought to form a layer beneath it to maintain the spherical or filamentous structure of the virion. The viral genome is enclosed in a shell mainly composed of a layer of M1 protein, HA and NA spikes, and the lipid envelope.

The genomes of influenza A and B viruses consist of eight single-stranded negative-sense RNA segments, while that of influenza C virus consists of seven RNA segments. Each viral RNA (vRNA) segment forms a ribonucleoprotein (RNP) complex which creates a twisted rod-like structure that is folded back and coiled on itself. The RNPs, but not the genomic RNA alone, are transcriptionally active. In the RNP complexes, the vRNA is associated with NP and a heterotrimeric RNA-dependent RNA polymerase complex that is composed of basic polymerase protein 1 (PB1), basic polymerase protein 2 (PB2), and acidic polymerase protein (PA). PB1 forms the core structure of the heterotrimeric RNA polymerase complex. The N-terminal region of PB1 binds to the C-terminal region of PA, and C-terminal region of PB1 binds to the N-terminal region of PB2.

Unlike most negative-sense RNA viruses, transcription and replication of the influenza virus genome occurs in the nucleus of infected cells. After synthesis of the genomic RNAs and viral proteins, RNPs are synthesized in nucleus and exported to the cytoplasm mediated by two viral proteins, M1 and nuclear export protein (NEP/NS2), through a cellular chromosome region maintenance 1 (Crm1) protein-dependent pathway. The RNPs are intracellularly transported to the budding site (i.e., the lipid rafts on the apical plasma membrane of polarized cells, while the transmembrane HA, NA, and M2 proteins are conveyed to the cell surface by the standard exocytic pathway. The RNPs are presumed to interact with the M1 proteins and/or the cytoplasmic tails of HA, NA, and M2 at the plasma membrane, to be packaged into virus particles. Finally, all of the viral components assemble into progeny virions, leading to budding from the apical plasma membrane by membrane fission.

SUMMARY

The present invention relates to new methods for preparing influenza virus from DNA constructs. The method combines elements of reverse genetics methods with classical reassortant techniques and the use of two or more distinct VLPs to produce a replication-competent fully infectious virus. The method includes the following: contacting a first population of host cells with plasmids or other vectors, e.g., adenovirus vectors, encoding the viral segments for, for example, 7 of the 8 influenza genomic segments or 8 of the 8 genomic segments where at least one of those 8 segments is modified so that a functional protein(s) is not expressed from that segment in a cell, as well as protein expression plasmids for the four influenza proteins to initiate viral replication and transcription and a host cell binding protein such as influenza HA protein, Ebola GP protein, rhabdovirus GP protein, or an antibody, including a chimeric protein, e.g., one having a cell membrane anchoring peptide from one source, such as HA2, fused to a host cell binding protein from a different source and that optionally lacks a cell membrane anchoring peptide. As used herein, a "viral segment" in a virus means an influenza vRNA sequence and a "viral segment" in a transcription cassette for production of a viral segment means a sequence that when introduced into a cell or appropriate cell-free system and transcribed, yields influenza vRNA or cRNA. Optionally, other protein product(s) corresponding to missing segment(s) may be expressed in the host cell, e.g., from a transfected plasmid owr as a stably integrated vector in the host genome, so that in one embodiment, one or more, and in another embodiment, the entire set of, proteins is available for viral replication. For example, viral proteins other than NS1 may be provided in trans. In one embodiment, the resulting VLPs carry less than the full genome of viral segments, e.g., only carry 1 or up to 7 of the 8 segments. In one embodiment, the resulting VLPs carry 8 of the 8 segments, where at least one of the segments is modified so that a functional protein(s) is not expressed from that segment in a cell. Accordingly, these VLPs can infect fresh cells (that lack the missing segment(s) or functional protein(s)), but will not undergo additional rounds of propagation due to the lack of the missing segment(s) or the functional protein(s)). Thus, the VLPs are infectious (bind to cells, enter cells and deliver viral RNA) but may be replication-incompetent. In parallel, another (second) population of cells is treated similarly, such that they are missing a different one of the 8 segments (for influenza A and B viruses) or lacking one of the 7 segments (for influenza C viruses) or have at least one modified segment that is not modified in the first population of cells, thereby producing distinct VLPs. For example, two populations of VLPs (e.g., a 7 segment VLP lacking the HA viral segment and a seven segment VLP lacking a PB2 viral segment) are mixed and inoculated into fresh cells. Some of the cells will become infected with both types of VLPs, with the result that all eight vRNAs will be produced or present in those cells, and infectious replicating influenza viruses will be generated. By matching the segments that are common between the two VLP populations, a predictable virus genome can be designed and produced. In some embodiments, fewer segments are included in the VLPs; for example, two sets of 4 segment VLPs, or 8 sets of 1segment VLPs, and the like, may be used; VLPs with mismatched numbers of segments may be combined, as long as the complete genome is represented in the pooled VLPs.

The invention thus provides a composition to prepare 1 and up to a 8 segment influenza A VLP. The composition includes one or more vectors which include at least one and up to eight transcription cassettes for production of at least one and up to eight influenza A virus segments (e.g., sequences for vRNA or for cRNA) selected from: a transcription cassette comprising a promoter operably linked to an influenza virus PA DNA, e.g., cDNA; a transcription cassette comprising a promoter operably linked to an influenza virus PB1 DNA, e.g., cDNA; a transcription cassette comprising a promoter operably linked to an influenza virus PB2 DNA, e.g., cDNA; a transcription cassette comprising a promoter operably linked to an influenza virus NP DNA, e.g., cDNA; a transcription cassette comprising a promoter operably linked to an influenza virus M DNA, e.g., cDNA; a transcription cassette comprising a promoter operably linked to an influenza virus NS DNA, e.g., cDNA; a transcription cassette comprising a promoter operably linked to an influenza virus NA DNA, e.g., cDNA; or a transcription cassette comprising a promoter operably linked to an influenza virus HA DNA or a non-influenza cell binding protein DNA, e.g., cDNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and a transcription cassette comprising a promoter operably linked to an influenza virus HA or a non-influenza virus cell binding protein DNA. If the one or more transcription cassettes for viral segment production do not include a transcription cassette comprising a promoter operably linked to an influenza virus M DNA, optionally a vector for mRNA production of M1 and M2 is included. If the one or more transcription cassettes for viral segment production do not include a transcription cassette comprising a promoter operably linked to an influenza virus NS DNA, optionally a vector for mRNA production of NS1 and NS2 is included. If the one or more transcription cassettes for vRNA do not include a transcription cassette comprising a promoter operably linked to an influenza virus NA DNA, optionally a vector for mRNA production of NA is included.

The invention also provides a composition to prepare 1 and up to a 8 segment influenza B VLP. The composition includes one or more vectors which include at least one and up to eight transcription cassettes for production of at least one and up to eight influenza B virus segments selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA and NB DNA; a transcription cassette comprising a promoter operably linked to an influenza virus HA DNA or non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and a transcription cassette comprising a promoter operably linked to an influenza virus HA or non-influenza virus cell binding protein DNA. If the one or more transcription cassettes for vRNA do not include a transcription cassette comprising a promoter operably linked to an influenza virus M DNA, optionally a vector for mRNA production of M1 and BM2 is included. If the one or more transcription cassettes for vRNA do not include a transcription cassette comprising a promoter operably linked to an influenza virus NS DNA, optionally a vector for mRNA production of NS1 and NS2 is included. If the one or more transcription cassettes for vRNA do not include a transcription cassette comprising a promoter operably linked to an influenza virus NA and NB DNA, optionally a vector for mRNA production of NA and optionally for NB is included.

The compositions may also include a vector for production of an additional viral segment, e.g., one that encodes a gene product of interest, e.g., a prophylactic or therapeutic protein such as an antigen of a microbe or a cancer antigen.

Further provided is an isolated host cell having the vectors for production of VLPs. In one embodiment, the host cell comprises one or more vectors which include at least one and up to eight transcription cassettes for production of at least one and up to eight influenza A virus segments selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA DNA; or a transcription cassette comprising a promoter operably linked to an influenza virus HA DNA or a non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and a transcription cassette comprising a promoter operably linked to an influenza virus HA or a non-influenza virus cell binding protein DNA. In one embodiment, if the one or more transcription cassettes for viral segment production do not include a transcription cassette comprising a promoter operably linked to an influenza virus M DNA, optionally a vector for mRNA production of M1 and M2 is included, wherein if the one or more transcription cassettes for vRNA do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA DNA, optionally a vector for mRNA production of NA is included. In one embodiment, the host cell is a recombinant host cell stably transformed with one or more vectors for mRNA production.

In one embodiment, the host cell comprises one or more vectors which include at least one and up to eight transcription cassettes for production of at least one and up to eight influenza B virus segments selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA and NB DNA; or a transcription cassette comprising a promoter operably linked to an influenza virus HA or non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus HA or non-influenza virus cell binding protein DNA, wherein if the one or more transcription cassettes for vRNA do not include a transcription cassette comprising a promoter operably linked to an influenza virus M DNA, optionally a vector for mRNA production of M1 and BM2 is included, wherein if the one or more transcription cassettes for vRNA do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA and NB DNA, optionally a vector for mRNA production of NA and optionally NB is included. In one embodiment, the host cell is a recombinant host cell stably transformed with one or more vectors for mRNA production.

Thus, in one embodiment, the invention provides a composition to prepare a 1 and up to 8 genomic segment influenza A or B VLP. In one embodiment, the composition includes one or more vectors which include at least one and up to eight transcription cassettes for production of at least one and up to eight viral segments from the genome of Influenza A virus selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA DNA; a transcription cassette comprising a promoter operably linked to an influenza virus HA DNA or a non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and a transcription cassette comprising a promoter operably linked to an influenza virus HA DNA or a non-influenza virus cell binding protein DNA.

The promoter or transcription termination sequence in a transcription cassette for viral segment or virus protein expression (mRNA production) may be the same or different relative to the promoter or transcription termination sequence in any other cassette. In one embodiment, the cassette which expresses an influenza viral genomic segment comprises a promoter suitable for expression in at least one particular host cell, e.g., avian or mammalian host cells such as canine, feline, equine, bovine, ovine, or primate cells including human cells, or for expression in more than one host.

In one embodiment, one or more transcription cassettes for production of a viral segment have a promoter including, but not limited to, a RNA polymerase I promoter, e.g., a human RNA polymerase I promoter, a RNA polymerase II promoter, a RNA polymerase III promoter, a T7 promoter, or a T3 promoter. For example, transcription termination sequences for the vectors include, but are not limited to, a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. Each promoter or transcription termination sequence in each transcription cassette may be the same or different than the promoters or transcription termination sequences in other cassettes. For instance, each RNA polymerase I promoter or transcription termination sequence in each transcription cassette may be the same or different as the RNA polymerase I promoter or transcription termination sequence in any other transcription cassette, each RNA polymerase II promoter or transcription termination sequence in each transcription cassette may be the same or different as the RNA polymerase II promoter or transcription termination sequence in any other transcription cassette, and each ribozyme sequence in each transcription cassette may be the same or different as the ribozyme sequences in any other cassette. In one embodiment, one or more transcription cassettes for vRNA comprise a RNA polymerase II promoter linked to a ribozyme sequence linked to viral coding sequences linked to another ribozyme sequences, optionally linked to a RNA polymerase II transcription termination sequence. In one embodiment, the ribozyme sequences in a single cassette are not the same. In one embodiment, at least 2 and more, e.g., 3, 4, 5, 6, or 7, transcription cassettes for viral segment production comprise a RNA polymerase II promoter, a first ribozyme sequence, which is 5' to a sequence corresponding to viral sequences including viral coding sequences, which is 5' to a second ribozyme sequence, which is 5' to a transcription termination sequence.

A plurality of the transcription cassettes of the invention may be physically linked or each transcription cassette may be present on an individual vector such as a plasmid or other, e.g., linear, nucleic acid delivery vehicle. In one embodiment, each transcription cassette is on a plasmid or a non-influenza viral vector. In one embodiment, one or more transcription cassettes are on one or more plasmids or a non-influenza viral vectors.

Further provided are methods of using vectors, compositions and host cells of the invention, e.g., to prepare a vaccine.

The invention provides a set of isolated host cells. The set includes a first host cell for producing a first VLP with at least 1 and up to 8 influenza A virus segments comprising: one or more vectors which include up to at least one and up to eight transcription cassettes for production of at least one and up to eight viral segments from the genome of influenza A virus selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA DNA; or a transcription cassette comprising a promoter operably linked to an influenza virus HA or non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and a transcription cassette comprising a promoter operably linked to an influenza virus HA or non-influenza virus cell binding protein DNA. If the one or more transcription cassettes for vRNA do not include a transcription cassette comprising a promoter operably linked to an influenza virus M DNA, optionally a vector for mRNA production of M1 and M2 is included, wherein if the one or more transcription cassettes for viral segment production do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA DNA, a vector for mRNA production of NA is included.

The second host cell for producing a second VLP with at least 1 and up to 8 influenza A virus segments includes one or more vectors which include at least one and up to seven transcription cassettes for production of at least one and up to eight viral segments from the genome of influenza A selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA DNA; a transcription cassette comprising a promoter operably linked to an influenza virus HA or non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus HA or non-influenza virus cell binding protein DNA. If the one or more transcription cassettes for vRNA do not include a transcription cassette comprising a promoter operably linked to an influenza virus M DNA, optionally a vector for mRNA production of M1 and M2 is included, wherein if the one or more transcription cassettes for vRNA do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA DNA, a vector for mRNA production of NA is included. In one embodiment, if the one or more transcription cassettes for viral segments in the second host cell do not include a transcription cassette comprising a promoter operably linked to an influenza virus M DNA, optionally a vector for mRNA production of M1 and M2 is included, wherein if the one or more transcription cassettes for viral segments do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA DNA, a vector for mRNA production of NA is included.

In one embodiment, in the set, the first host cell has at least one transcription cassette for expression of at least one viral segment that is not present in the second host cell and the second host cell has at least one transcription cassette for expression of at least one viral segment that is not present in the first host cell. In one embodiment, the first host cell has 7 of the expression cassettes for viral segment production and the second host cell has 7 of the expression cassettes for viral segment production. In one embodiment, the first host cell has at least 2 of the expression cassettes for viral segment production and the second host cell has at least 6 of the expression cassettes for viral segment production. In one embodiment, the first host cell has at least 3 of the expression cassettes for viral segment production and the second host cell has at least 5 of the expression cassettes for viral segment production. In one embodiment, the first host cell has at least 4 of the expression cassettes for vRNA production and the second host cell has at least 4 of the expression cassettes for viral segment production. In one embodiment, the first host cell has at least 5 of the expression cassettes for viral segment production and the second host cell has at least 3 of the expression cassettes for viral segment production. In one embodiment, the first host cell has at least 6 of the expression cassettes for viral segment production and the second host cell has at least 2 of the expression cassettes for viral segment production. In one embodiment, the first host cell has less than 7 of the expression cassettes for viral segment production and the second host cell has less than 7 of the expression cassettes for viral segment production. In one embodiment, if the transcription cassettes for viral segments in the first and second host cells do not include all 8 viral segments, the set further comprises one or more host cells that each produce a VLP with viral segment(s) that is/are not present in the set.

Further provided is an isolated VLP having at least one and up to 8 influenza A virus segments. The VLP has one and up to eight influenza A virus segments selected from: an influenza virus PA segment; an influenza virus PB1 segment; an influenza virus PB2 segment; an influenza virus NP segment; an influenza virus M segment; an influenza virus NS segment; an influenza virus NA segment; or an influenza virus HA segment or a HA segment modified to include a non-influenza virus cell binding protein; and wherein the VLP comprises PA, PB1, PB2, NP, and HA or a non-influenza virus cell binding protein.

Further provided is an isolated VLP having at least one and up to 7 influenza A virus segments. The VLP has one and up to seven influenza A virus segments are selected from: an influenza virus PA segment; an influenza virus PB1 segment; an influenza virus PB2 segment; an influenza virus NP segment; an influenza virus M segment; an influenza virus NS segment; an influenza virus NA segment; or an influenza virus HA segment or a HA segment modified to include a non-influenza virus cell binding protein; and wherein the VLP comprises PA, PB1, PB2, NP, and HA or a non-influenza virus cell binding protein.

Also provided is a set of isolated VLPs, wherein one VLP in the set has: one or up to eight influenza A virus segments selected from: an influenza virus PA segment; an influenza virus PB1 segment; an influenza virus PB2 segment; an influenza virus NP segment; an influenza virus M segment; an influenza virus NS segment; an influenza virus NA segment; or an influenza virus HA or a modified HA segment having sequences for a non-influenza host cell binding protein; and wherein the VLP comprises PA, PB1, PB2, NP, and HA or a non-influenza host cell binding protein; and wherein a second VLP in the set has one and up to eight influenza A virus viral segments selected from: an influenza virus PA segment; an influenza virus PB1 segment; an influenza virus PB2 segment; an influenza virus NP segment; an influenza virus M segment; an influenza virus NS segment; an influenza virus NA segment; or an influenza virus HA segment or a modified HA segment having sequences for a non-influenza host cell binding protein; and wherein the second VLP comprises PA, PB1, PB2, NP, and HA or a non-influenza host cell binding protein; wherein the first VLP has at least one segment that is not present in the second VLP or wherein the first VLP has at least one segment that is modified in the second VLP so that a functional influenza virus protein is not expressed from that modified segment. In one embodiment, the second VLP has at least one viral segment that is not present in the first VLP. In one embodiment, at least one of the VLPs further comprises an influenza viral segment comprising 3' influenza virus noncoding sequences linked to non-influenza sequences linked to 5' influenza virus noncoding sequences.

Also provided is a method to prepare influenza A virus. The method includes infecting a host cell with at least two different VLPs, wherein the VLPs include a first isolated VLP having at least one and up to 8 influenza A virus segments and a second VLP having at least one and up to 8 influenza A virus segments. The first VLP and the second VLP comprise one and up to eight influenza A virus segments selected from: an influenza virus PA segment; an influenza virus PB1 segment; an influenza virus PB2 segment; an influenza virus NP segment; an influenza virus M segment; an influenza virus NS segment; an influenza virus NA segment; or an influenza virus HA segment or a modified HA segment having sequences for a non-influenza virus cell binding protein; and wherein the first VLP and the second VLP comprise PA, PB1, PB2, NP, and HA or a non-influenza virus cell binding protein. In one embodiment, the first VLP has at least one viral segment that is modified in the second VLP to not encode a functional influenza virus protein. In one embodiment, the first VLP has at least one viral segment that is not present in the second VLP and the second VLP has at least one viral segment that is not present in the first VLP. In one embodiment, at least one of the segments of the first VLP is from the same virus isolate as the corresponding segment in the second VLP. In one embodiment, at least one of the segments of the first VLP is from a different virus isolate as the corresponding segment in the second VLP. In one embodiment, the first VLP has 7 segments and the second VLP has 7 segments. In one embodiment, the first VLP has 7 segments and the second VLP has 6 segments. In one embodiment, the first VLP has at least 3 segments and the second VLP has 7 segments. In one embodiment, the first VLP has at least 4 segments and the second VLP has at least 4 segments. In one embodiment, the first VLP has less than 7 segments and the second VLP has less than 7 segments. In one embodiment, if the segments in the first and second VLPs do not include all 8 vRNAs, the host cell is further infected with one or more other VLPs that have a segment(s) that is/are not present in the first and second VLPs. In one embodiment, the first VLP has less than 8 viral segments. In one embodiment, the second VLP has less than 8 viral segments.

The invention further provides a set of isolated host cells. In one embodiment, the set includes a first host cell for producing a first VLP with less than 8 influenza B virus segments comprising: one or more vectors which include up to at least one and up to seven transcription cassettes for vRNA production of at least one and up to seven viral segments from the genome of Influenza B virus selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA and NB DNA; or a transcription cassette comprising a promoter operably linked to an influenza virus HA DNA or non-influenza virus cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus HA or non-influenza virus cell binding protein DNA. If the one or more transcription cassettes for vRNA do not include a transcription cassette comprising a promoter operably linked to an influenza virus M DNA, optionally a vector for mRNA production of M1 and BM2 is included, wherein if the one or more transcription cassettes for vRNA do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA and NB DNA, optionally a vector for mRNA production of NA and NB is included.

In one embodiment, the second host cell for producing a second VLP with less than 8 influenza B virus segments includes one or more vectors which include at least one and up to seven transcription cassettes for vRNA production of at least one and up to seven viral segments from the genome of influenza B selected from: a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; a transcription cassette comprising a promoter operably linked to an influenza virus M DNA; a transcription cassette comprising a promoter operably linked to an influenza virus NS DNA; a transcription cassette comprising a promoter operably linked to an influenza virus NA and NB DNA; a transcription cassette comprising a promoter operably linked to an influenza virus HA DNA or a non-influenza host cell binding protein DNA; and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and a transcription cassette comprising a promoter operably linked to an influenza virus HA or a non-influenza host cell binding protein DNA. If the one or more transcription cassettes for vRNA do not include a transcription cassette comprising a promoter operably linked to an influenza virus M DNA, optionally a vector for mRNA production of M1 and BM2 is included, wherein if the one or more transcription cassettes for vRNA do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA and NB DNA, optionally a vector for mRNA production of NA and NB is included.

In the set, in one embodiment, the first host cell has at least one transcription cassette for expression of at least one viral segment that is not present in the second host cell and the second host cell has at least one transcription cassette for vRNA expression of at least one viral segment that is not present in the first host cell. In one embodiment, the first host cell has 7 of the expression cassettes for viral segment production and the second host cell has 7 of the expression cassettes for viral segment production. In one embodiment, the first host cell has at least 2 of the expression cassettes for viral segment production and the second host cell has at least 6 of the expression cassettes for viral segment production. In one embodiment, the first host cell has at least 3 of the expression cassettes for viral segment production and the second host cell has at least 5 of the expression cassettes for viral segment production. In one embodiment, the first host cell has at least 4 of the expression cassettes for viral segment production and the second host cell has at least 4 of the expression cassettes for viral segment production. In one embodiment, the first host cell has at least 5 of the expression cassettes for viral segment production and the second host cell has at least 3 of the expression cassettes for viral segment production. In one embodiment, the first host cell has at least 6 of the expression cassettes for viral segment production and the second host cell has at least 2 of the expression cassettes for viral segment production. In one embodiment, the first host cell has less than 7 of the expression cassettes for viral segment production and the second host cell has less than 7 of the expression cassettes for viral segment production. In one embodiment, if the transcription cassettes for vRNA in the first and second host cells do not include all 8 viral segments, the set further comprises one or more host cells that each produce a VLP that have the viral segment (s) that is/are not present in the set.

Further provided is an isolated VLP having less than 8 influenza B virus segments. The VLP has one and up to seven influenza B virus segments selected from: an influenza virus PA segment; an influenza virus PB1 segment; an influenza virus PB2 segment; an influenza virus NP segment; an influenza virus M segment; an influenza virus NS segment; an influenza virus NA and NB segment; or an influenza virus HA segment or modified HA segment having sequences encoding a non-influenza cell binding protein; and wherein the VLP comprises PA, PB1, PB2, NP, and HA or a non-influenza cell binding protein.

Also provided is a method to prepare influenza B virus. The method includes infecting a host cell with at least two different VLPs, wherein the VLPs include a first isolated VLP having less than 8 influenza B virus segments and a second VLP having less than 8 influenza A virus segments. The first VLP and the second VLP comprise one and up to seven influenza B virus segments selected from: an influenza virus PA segment; an influenza virus PB1 segment; an influenza virus PB2 segment; an influenza virus NP segment; an influenza virus M segment; an influenza virus NS segment; an influenza virus NA segment; or an influenza virus HA segment; and wherein the first VLP and the second VLP comprise PA, PB1, PB2, NP, and HA. The first VLP has at least one viral segment that is not present in the second VLP, and wherein the second VLP has at least one viral segment that is not present in the first VLP. In one embodiment, at least one of the segments of the first VLP is from the same virus isolate as the corresponding segment in the second VLP. In one embodiment, at least one of the segments of the first VLP is from a different virus isolate as the corresponding segment in the second VLP. In one embodiment, the first VLP has 7 segments and the second VLP has 7 segments. In one embodiment, the first VLP has 7 segments and the second VLP has 6 segments. In one embodiment, the first VLP has at least 3 segments and the second VLP has 7 segments. In one embodiment, the first VLP has at least 4 segments and the second VLP has at least 4 segments. In one embodiment, the first VLP has less than 7 segments and the second VLP has less than 7 segments. In one embodiment, if the segments in the first and second VLPs do not include all 8 vRNAs, the host cell is further infected with one or more other VLPs with less than 8 influenza B virus segments but that have a segment that is not present in the first and second VLPs.

Similar compositions, host cells and methods may be employed for influenza C virus, e.g., to prepare a VLP that has one and up to 7 of the influenza C virus segments.

DETAILED DESCRIPTION

Definitions

A "VLP" as used herein is an influenza virus-like particle containing 1 or up to 8 (for influenza A and B viruses) or 1 or up to 7 (for influenza C viruses) influenza viral genomic segments. In one embodiment, the VLP has less than 8 genomic segments (for influenza A and B viruses) or less than 7 genomic segments (for influenza C viruses). A VLP can infect a cell but by itself cannot produce progeny virus unless something is provided in trans, e.g., by providing a complementing VLP. In one embodiment, the VLP has less than 8 genomic segments (for influenza A and B viruses) and each of those influenza A virus or influenza B virus segments has sequences that encode functional influenza virus protein(s). In one embodiment, the VLP has less than 7 genomic segments (for influenza C viruses) and each of those influenza C virus segments has sequences that encode functional influenza virus protein(s). In one embodiment, if more than 1 genomic segment is present, at least one influenza viral genomic segment may not encode a functional version of the main viral protein(s) encoded by the respective segment (i.e., the PB2, PB1, PA, HA, NP, NA, M1, M2, NS1, NS2 proteins), e.g., as a result of modification of the genomic segment, for instance, via deletion, insertion or substitution of one or more nucleotides. In one embodiment, a VLP may have the same number of viral segments as a wild-type influenza virus, e.g., for influenza A or B that is 8 segments, but at least one segment in the VLP is non-functional, e.g., does not express a viral protein for replication or packaging, or for infectious virus production. In addition to one or more viral genomic segment(s), the VLPs may comprise at least a protein required for binding to host cells (for example, the influenza virus HA protein, the Ebola virus GP protein, or the VSV G protein), and the viral proteins required for viral RNA replication and transcription (i.e., the PB2, PB1, PA, and NP proteins which, together with the viral RNA, form the viral ribonucleoprotein complex). Most VLPs will be replication incompetent (i.e., dependent on a helper function). Some VLPs may be replication competent (i.e., they may lack the capability to express an influenza viral protein such as NA or NS1, but may still be able to form infectious progeny viruses). A replication competent VLP may be attenuated. A set of VLPs may be used to co-infect cells and yield a replication competent influenza virus so long as the set includes at least one "functional segment" (defined as a segment encoding functional PB2, PB1, PA, HA, NP, NA or NB, M1, M2, NS1, or NS2 protein) for each of the 8 segments for type A or type B or at least one functional segment for each of the 7 segments for type C.

As used herein, the terms "isolated" refers to in vitro preparation, isolation of a nucleic acid molecule such as a vector or plasmid of the invention or a virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome, e.g., deletion of sequences or entire segments, or otherwise artificially generated. As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Negative-Sense RNA Viruses

Negative-sense RNA viruses are classified into seven families (*Rhabdoviridae, Paramyxoviridae, Filoviridae, Bornaviridae, Orthomyxoviridae, Bunyaviridae,* and *Arenaviridae*) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, noncoding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

Influenza viruses are orthomyxoviruses. Influenza A viruses possess a genome of eight single-stranded negative-sense viral RNAs (vRNAs) that encode a total of at least ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase ("HEF") rather than individual HA and NA proteins.

Influenza Vaccines

Current vaccines for seasonal influenza are trivalent—they contain two influenza A virus strains of the H3N2 and H1N1 subtypes and an influenza B virus, or quadrivlent. On average, these vaccines are updated every 2-3 years due to accumulated point mutations in the HA and NA proteins that allow the viruses to evade the human immune response. Current influenza vaccines are either inactivated or live attenuated vaccines. Inactivated vaccines dominate the influenza virus vaccine market and are made from reassortant viruses that contain genes encoding the surface proteins of the predominant or targeted strain, most notably the HA gene and the NA gene. These viruses are typically overproduced in chicken eggs and then chemically treated, e.g., with formaldehyde, to inactivate them. The introduction of the inactivated but intact virions induces an immune response specific for the combination of HA and NA (also referred to as H and N, e.g., H5N1).

Until recently, inactivated virus preparations were the only influenza vaccines available. Most inactivated vaccines are safe and elicit a humoral, but not a strong cellular, immune response. To produce seed strains, embryonated chicken eggs are co-infected with the epidemic strain and A/Puerto Rico/8/34(H1N1) (PR8) virus, which provides high-growth properties. For influenza B virus vaccine production, a field strain is used to provide the virus backbone. Virus populations are screened for reassortants that contain the HA and NA genes of the epidemic strain and grow well in eggs. Once an appropriate vaccine seed virus is selected, it is amplified in eggs, purified, and treated to generate inactivated, split (i.e., disrupted), or subunit (i.e., partially purified by the removal of viral ribonucleoprotein complexes) vaccines. Vaccine quantities are then standardized and adjusted to 15 µg HA per strain.

The efficacy of inactivated influenza vaccines typically ranges from 60% to 90% in healthy adults younger than 65 years of age (Beyer et al., 2002). It can, however, be significantly lower in young children (Smith et al., 2006) due to their naive immune status and in the elderly (Gross et al., 1995; Nichol et al., 1998) due to their decreased immune function, thus leaving two major risk groups partially unprotected.

Live but attenuated vaccines are more controversial because in some scenarios they involve live virus which is shed by the patient for several weeks, although they elicit both humoral and cellular immune responses. This live virus contains mutations such that while it can replicate, it is not supposed to be virulent, i.e., is not supposed to cause disease.

Reverse Genetic Technologies for Influenza Vaccine Production

The production of both inactivated and live influenza vaccines relies on the isolation of reassortant viruses with certain gene constellations. The co-infection of cells with two different influenza A or B viruses yields $2^8=256$ different gene combinations, making the isolation of the desired reassortant cumbersome. In 1999, a system was developed that allows the artificial generation of influenza viruses from cloned cDNA (Neumann et al., 1999). In this approach, cells are co-transfected with plasmids that encode the influenza vRNAs and plasmids that encode the components of the viral replication complex (i.e., the polymerase and NP proteins). The former plasmids contain a promoter for vRNA production, e.g., an RNA polymerase I promoter sequence, a cDNA encoding a full-length viral RNA in the negative-sense orientation, and a RNA terminator sequence, e.g., an RNA polymerase I terminator sequence. Intracellular transcription by RNA polymerase I yields transcripts identical to influenza viral RNAs that can therefore be amplified by the viral polymerase and nucleoproteins. Forty-eight hours post-transfection, up to $10^8$ infectious viruses are detected per ml of cell culture supernatant. This system allows the introduction of any (viable) mutation into the influenza viral genome. Moreover, tailor-made reassortant viruses can be generated using this system. To produce vaccine viruses, cells can be transfected with 2 plasmids encoding the HA and NA genes of the epidemic strain and 6 plasmids encoding the internal genes of either PR8 virus (for the production of inactivated vaccine) or attenuated A/Ann Arbor/6/60 virus (for the production of live attenuated virus). As described herein, reverse genetics is the basis for the development of live, attenuated influenza virus vaccines that lack NA activity and optionally contain mutations in other viral genes, e.g., mutations in the HA gene that reduce the pathogenic potential of the resulting virus.

The amino acid composition at the HA cleavage site is recognized as a determinant of virulence for influenza viruses (Bosch et al., 1979). Highly pathogenic avian influenza viurses (HPAI) contain multiple basic amino acids at their HA cleavage site (Kawaoka et al., 1984) that are recognized by ubiquitous cellular proteases (Horimoto et al., 1997; Stieneke-Grober et al., 1998), which leads to systemic infection. By contrast, viruses with low pathogenicity contain a single arginine residue at the HA cleavage site (Kawaoka et al., 1984), which is cleaved in only a few organs, resulting in localized infection. Multiple basic amino acids at the HA cleavage site may be associated with virulence, as replacement of the 'virulent-type' HA cleavage site with an 'avirulent-type' HA cleavage site converted a highly pathogenic avian influenza virus into a low pathogenic variant (Horimoto et al., 1990). Thus, highly pathogenic avian influenza viruses can be converted to low pathogenic forms by replacing the 'virulent-type' HA cleavage sequence with an 'avirulent-type' sequence (Horimoto et al., 1994). These 'detoxifying' mutations can be introduced into viral genomes to generate candidate vaccines that contain attenuated H5 virus HA genes in a background of, for example, high-growth PR8 virus.

The Structure of RNPS Inside Virions

The conformation of RNPs inside virions had been the source of considerable controversy. When examined by negative staining, a continuous strand 7-8 nm in diameter is arranged in the form of a helix within disrupted virions. The helices vary considerably from virion to virion with respect to the number of turns and overall diameter. Because the continuous strand had been the only structure seen within the virions by negative staining, it was thought to represent the natural organization of the viral RNP. Thus, it was proposed that the viral RNP exists as a single continuous helix within the virions and that the continuous helix would be fragmented into multiple RNPs during the purification process. However, it is difficult to morphologically reconcile the single continuous helix with the twisted rod-like structures seen when RNPs are extracted from virions. In addition, there is no evidence that the continuous helices are actually composed of NP molecules. Later, it was revealed, by negative staining electron microscopy, that a wide variety of the continuous helices within virions consist of the same units that have a dimension of 4 by 4 nm. They also demonstrated that isolated M1 protein formed regular strands on liposomes when it was reassociated with lipids in vitro. Because influenza virus has two major internal proteins, NP and M1, and the NP monomer has dimensions of 6.2 by 3.5 nm, they concluded that the 4 nm×4 nm unit represents an M1 molecule. Thus, the continuous helices of 7-8 nm in diameter seen in the negatively stained disrupted virions are probably pairs of M1 strands, representing a layer of M1 proteins underneath the lipid envelope. It is possible that similar continuous helices observed in purified virions by cryoelectron microscopy also represent the layer of M1 molecules.

One explanation for the difficulty in elucidating the internal structure of influenza virions by negative staining electron microscopy may originate with poor penetration of stain solutions. To observe the RNPs inside virions by negative staining electron microscopy, purified virions were briefly treated with trypsin to partially remove glycoproteins on the envelope. The trypsin-treated virions were infectious and had HA activity but were devoid of NA activity. Irregularly compressed rod-like structures with diameters similar to those of mid-sectioned RNPs extracted from virions were observed inside these trypsin-treated virions. Further, twisted rod-like structures, which were morphologically identical to purified RNPs, "spilled" from some of the trypsin-treated virions. Such twisted rod-like structures also protruded from virions disrupted by freeze-drying and reacted with anti-NP monocional antibodies, suggesting that the RNPs exist within the virions as fragmented rod-like structures. Thin-section electron microscopy of purified virions also supports this notion. Thin-section electron microscopy of purified virions showed some compressed rod-like structures of 10-13 nm in diameter inside the virions, which were morphologically similar to both the purified RNPs and the RNPs seen in trypsin-treated virions by negative staining electron microscopy. The good agreement between images obtained by negative staining of purified virions and those obtained by thin sectioning of pelleted virions suggests that the RNPs are present as separate rod-like structures within intact virions.

Arrangement of RNPS Inside a Virion

It remains unclear how the fragmented RNPs are organized within the virions. Once this issue is resolved, we will finally be able to elucidate the genome packaging mechanism by which vRNA segments are incorporated into each virion. In early proposals, it was predicted that the vRNA segments were bound to a single backbone for cooperative packaging of the segmented vRNAs. However, because this idea is based on the electron microscopic observations of the single continuous helix seen in negatively stained disrupted virions, which has since been shown to represent the layer of M1 molecules, it is an unlikely scenario. Information about the organization of the fragmented rod-like RNPs within the virions is limited.

It was demonstrated by thin-section electron microscopy that elongated virions budding from the plasma membrane of infected cells contain distinct arrangement of RNPs inside. When the elongated budding virions were sectioned longitudinally, nearly all of them contained rod-like RNPs that were always suspended from the interior of the viral envelope at the distal end of the elongated virions and were oriented perpendicular to the budding tip. They were about 12 nm in width and up to 130 nm in length, consistent with the size of purified RNPs. RNPs were similarly observed not only in budded virions but also virions in the course of budding, suggesting that the incorporation of fragmented RNPs is coordinated with bud growth. In transversely sectioned budding virions, electron-dense dots of about 12 nm in diameter, confirmed as RNPs by immunoelectron microscopy with anti-NP monocional antibodies, were observed. These dots represent-cross sections of the rod-like RNPs and were apparent inside each budding virion. Interestingly, we found that many of the transversely sectioned budding virions contained a regular arrangement of eight RNPs, in which a central RNP was surrounded by seven others (7+1) configuration. No more than eight RNPs were observed in a virion in our study. Notably, serial transverse sections of whole budding virions revealed that all budding virions contained the maximum of eight RNPs, but that they differed in length. Because the length of the RNPs correlates with the length of each vRNA segment [6], these results suggest that each virion contains a highly organized set of eight RNPs composed of different kinds of vRNA segments. The (7+1) configuration of the eight RNPs was also observed in huge filamentous virions as well as different viruses isolated from humans, pigs, and birds. Some transversely sectioned filamentous virions showed the typical configuration of eight RNPs, although most were empty. In the longitudinal sections, the RNPs were confined to the distal end of each filamentous virion and the set of eight RNPs. These results suggest that all budding virions, independent of the virion shape, incorporate an organized set of eight fragmented RNPs that are associated with the inner envelope at the distal end of the virion.

In contrast, isolated virions released into environmental solution and purified by ultracentrifugation showed a somewhat different organization of the RNPs within the virions. In an earlier report, the internal structures of purified virions, which were uniformly spherical at approximately 100 nm in diameter, were examined by thin-section electron microscopy. Thin-sections of virion pellets showed a wide variety of organization patterns of compressed rod-like RNPs in most of the purified virions, although some virions exhibited the (7+1) configuration of the RNPs. In theory, when the rod-like RNPs are perpendicular to the electron beam, rod-like structures are observed in the virions. On the other hand, when the rod-like RNPs are parallel to the electron beam, round dots are observed in the virions. Because the purified virions are randomly oriented with respect to the electron beam in the pellets, it is natural that only some particles show the (7+1) configuration of eight RNPs. In addition, because some RNPs (from approximately 30 to 120 nm in length) are larger than typical spherical virions (approximately 80-120 nm in diameter, including surface spikes), it is possible that some RNPs are compressed and the configurations they had at the time of budding are partially destroyed within the spherical virions. Therefore, it is conceivable that the spherical virions after purification show disordered arrangements of RNPs as well as the regular arrangement of eight RNPs, while the elongated budding virions on the cell surface show the (7+1) configuration within the virions when they are transversely sectioned. Taken together, it appears that the eight fragmented RNPs hold the well-organized configuration when the virions are budding, but this configuration becomes partially distorted or completely destroyed within the spherical virions upon detachment from the cell surface.

Recently, detailed internal structures of purified virions was resolved by cryoelectron tomography. Although they also found the (7+1) configuration of eight RNPs within the purified virions, the eight RNPs were not that well aligned in most virions and the (7+1) configuration was observed at only a low frequency. Such disordered arrangement of the eight RNPs, as well as the limited observation of the (7+1) configuration, suggests that the purified virions were randomly oriented to the electron beam and that some RNPs were compressed in spherical virions, as described above. It was also noted that, in their experiment, the purified virions were substantially pleomorphic, differing in size and shape, and that most of the virions contained fewer than eight RNPs. They concluded that the incorporation of a complete set of eight RNPs may not occur in each virion and that the arrangement of fragmented RNPs within virions may not be uniform from virion to virion. These discrepancies between budding virions and purified virions could arise from the difference in virion morphology that accompanies sample processing for virion purification. Budding virions on the plasma membrane of infected cells show relatively regular structure, such as elongated or huge filamentous particles with uniform diameter, and are not pleomorphic. On the other hand, purified virions show not only typical spherical structures but also pleomorphic structures of different sizes which have never been reported on thin-section or scanning electron microscopy of budding virions at the plasma membrane. Because morphological changes readily occur in released virions, even when they are kept for a few days at 48° C. during the purification process, these pleomorphic particles seen only in purified samples could be artifacts introduced during purification. These pleomorphic particles cannot, therefore, reflect the native structure of the virions as the arrangement of RNPs in these particles would be altered.

A Possible Mechanism of Genome Packaging

Two models have been proposed thus far to explain the mechanism by which vRNA segments are packaged into virions: the random packaging and selective packaging models. The former model assumes a common packaging signal in all vRNA segments, which differentiates between vRNAs and cellular RNAs but not among vRNAs, enabling any number and combination of vRNAs to be incorporated randomly into virions. The selective packaging model predicts the presence of specific packaging signals for each vRNA segment, which differentiate not only between vRNAs and cellular RNAs but also between individual vRNAs, leading to the incorporation of a complete set of eight vRNA segments into virions. Conclusive evidence in support of either model is lacking, and controversy over the mechanism of genome packaging ensues. Recently, by virtue of reverse genetics, it was revealed that all of the eight vRNA segments possess segment-specific packaging signals for efficient incorporation into virions. These packaging signals include bipartite sequences at the 5' and 3' ends of the vRNA, which house not only conserved promoter sequences but also coding and segment-specific non-coding regions adjacent to the promoter region. These findings, together with electron microscopic observations of the influenza virion interior, support the selective packaging model and refute the random packaging model.

The (7+1) configuration of eight RNPs observed in virions likely requires specific interactions among the vRNAs (RNPs) to stably maintain the configuration. Reverse genetics studies showed that mutations or deletions in a packaging signal of a vRNA segment reduced incorporation of the other vRNA segments into virions, suggesting that incorporation of the eight vRNA segments are unlikely to be independent but, rather coordinated events involving inter-segment interactions. However, it remains uncertain whether there are specific interactions among the eight RNPs in virions. The physical contacts among the eight RNPs observed in tomograms of transversely sectioned budding virions provides potential morphological evidence supporting the presence of interactions among RNPs [54]. Because the vRNA is wrapped around the NP scaffold, such contacts may represent vRNA-vRNA interactions through the packaging signals in the respective vRNA segments that are necessary for efficient incorporation into virions. Although speculative, the interactions among RNPs though the packaging signals may contribute to recruitment of a complete set of eight RNPs as well as the (7+1) configuration. Elucidation of the fine structure of RNPs within virions, as well as the three-dimensional position of the packaging signals on RNPs, could provide the missing details of the packaging mechanism of the influenza virus genome.

Exemplary Vectors of the Invention

In one embodiment, the invention provides one or more isolated vectors, or a composition which includes one or more isolated vectors, having a plurality of transcription cassettes for influenza vRNA (viral segment) production and influenza virus mRNA for protein production, but less than the full complement of the viral genome of segments or having a viral segment that does not encode at least one functional influenza virus protein. The vector(s) or composition includes, in one embodiment, one or more vectors having a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA.

In one embodiment, a vector of the invention may include two or more transcription cassettes selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and a transcription cassette comprising a PolI promoter operably linked to an influenza virus M cDNA, e.g., a full-length influenza virus M cDNA, linked to a PolI transcription termination sequence.

In one embodiment, a vector of the invention includes two or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and a transcription cassette comprising a PolII promoter operably linked to a DNA coding region for influenza virus NP linked to a PolII transcription termination sequence.

The invention further includes a vector with at least two transcription cassettes selected from a transcription cassette comprising a PolI promoter and a PolI transcription termination sequence and a PolII promoter and a PolII transcription termination sequence each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA.

The invention also provides one or more isolated vectors having a plurality of transcription cassettes: one or more vectors having a transcription cassette comprising a PolII promoter linked to a ribozyme sequence linked to an influenza virus PA cDNA, e.g., a full-length influenza virus PA cDNA, linked to a ribozyme sequence linked to a PolII transcription termination sequence, a transcription cassette comprising a PolII promoter linked to a ribozyme sequence linked to an influenza virus PB1 cDNA, e.g., a full-length influenza virus PB1 cDNA, linked to a ribozyme sequence linked to a PolII transcription termination sequence, a transcription cassette comprising a PolII promoter linked to a ribozyme sequence linked to an influenza virus PB2 cDNA, e.g., a full-length influenza virus PB2 cDNA, linked to a ribozyme sequence linked to a PolII transcription termination sequence, a transcription cassette comprising a PolII promoter linked to a ribozyme sequence linked to an influenza virus HA cDNA, e.g., a full-length influenza virus HA cDNA, linked to a ribozyme sequence linked to a PolII transcription termination sequence, a transcription cassette comprising a PolII promoter linked to a ribozyme sequence linked to an influenza virus NP cDNA, e.g., a full-length influenza virus NP cDNA, linked to a ribozyme sequence linked to a PolII transcription termination sequence, a transcription cassette comprising a PolII promoter linked to a ribozyme sequence linked to an influenza virus M cDNA, e.g., a full-length influenza virus M cDNA, linked to a ribozyme sequence linked to a PolII transcription termination sequence, a transcription cassette comprising a PolII promoter linked to a ribozyme sequence linked to an influenza virus NS cDNA, e.g., a full-length influenza virus NS cDNA, linked to a ribozyme sequence linked to a PolII transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA.

In one embodiment, the use of certain plasmid vectors significantly reduces the number of plasmids required for the generation of segmented virus such as influenza virus, increases the rescue efficiency of influenza virus in cell lines that can be transfected with high efficiencies, and/or allows for the generation of influenza virus in cell lines that cannot be transfected with high efficiencies, including cell lines for the production of human vaccines (e.g., Vero cells). Accordingly, the use of the vectors of the invention reduces the number of variables for virus generation, resulting in more consistent generation of influenza virus, and decreasing the burden of providing proper documentation of plasmid history, purity, and toxicity. These advantages allow the speedy generation of vaccine viruses, especially for pandemics.

Exemplary Compositions of the Invention

The invention provides a composition comprising at least one vector, e.g., at least one plasmid, which includes one or more transcription cassettes for vRNA production (but in one embodiment less than the full complement of vRNAs) or cRNA production selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and/or a transcription cassette comprising a PolI promoter operably linked to an influenza virus NS cDNA, e.g., a full-length influenza virus NS cDNA, linked to a PolI transcription termination sequence; and at least one vector, e.g., at least one plasmid, which includes one or more transcription cassettes for mRNA production selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, each PolI promoter is the same. In one embodiment, each PolII promoter is the same. In one embodiment, each PolI transcription terminator sequence is the same. In one embodiment, each PolII transcription terminator sequence is the same.

In one embodiment, at least one vector, e.g., plasmid or a viral vector including but not limited to an adenovirus (see, e.g., U.S. Pat. No. 8,043,856, the disclosure of which is incorporated by reference herein) adeno-associated virus (AAV), poxvirus, papillomavirus, lentivirus, herpesvirus, foamivirus or retrovirus vectors, includes transcription cassettes for one or more of influenza virus PA, influenza virus PB1, influenza virus PB2, influenza virus HA, influenza virus NP, influenza virus M, and influenza virus NS segments. In one embodiment, at least one plasmid for mRNA production includes transcription cassettes for one or more of influenza virus PA, influenza virus PB1, influenza virus PB2 or influenza virus NP, e.g., the at least one plasmid for mRNA production includes cassettes for influenza virus PA, influenza virus PB1, influenza virus PB2 and influenza virus NP. In one embodiment, one plasmid for mRNA production includes three of the cassettes, wherein the composition further comprises another plasmid for mRNA production with a PolII promoter operably linked to a DNA coding region for an influenza virus gene linked to a PolII transcription termination sequence. For instance, one plasmid for mRNA production includes transcription cassettes for influenza virus PA, influenza virus PB1, influenza virus PB2 and another plasmid includes a transcription cassette for influenza virus NP. In another embodiment, at least one plasmid for vRNA production includes transcription cassettes for influenza virus PA, influenza virus PB1, influenza virus PB2, influenza virus NP, influenza virus M, and influenza virus NS. Also included is a plasmid for vRNA production which includes a transcription cassette comprising a PolI promoter operably linked to an influenza virus HA cDNA, e.g., a full-length influenza virus HA cDNA, linked to a PolI transcription termination sequence. For instance, one plasmid for mRNA production includes cassettes for influenza virus PA, influenza virus PB1, influenza virus PB2 and influenza virus NP. In another embodiment, one plasmid for mRNA production includes three of the cassettes, wherein the composition further comprises another plasmid for mRNA production with a PolII promoter operably linked to a DNA coding region for an influenza virus gene linked to a PolII transcription termination sequence, wherein the DNA coding region is for an influenza virus gene that is not on the plasmid which includes the three cassettes, e.g., the at least one plasmid for mRNA production includes cassettes for influenza virus PA, influenza virus PB1, influenza virus PB2 and the other plasmid includes a cassette for influenza virus NP.

In one embodiment, a composition of the invention comprises a vector which includes up to seven transcription cassettes selected from: a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NA cDNA (or NA and NB cDNA), e.g., a full-length influenza virus NA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, and a transcription cassette comprising a PolI promoter operably linked to an influenza virus NS cDNA, e.g., a full-length influenza virus NS cDNA, linked to a PolI transcription termination sequence. In one embodiment, the HA in a transcription cassette is a type A HA. In another embodiment, the HA in a transcription cassette is a type B HA. In one embodiment, the RNA polymerase I promoter is a human RNA polymerase I promoter. In one embodiment, the composition includes transcription cassettes comprising a PolI promoter operably linked to an influenza virus DNA sequence for M1 and BM2 or for both M1 and M2, linked to a PolI transcription termination sequence.

Also provided a composition comprising a vector which includes one or more transcription cassettes selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence.

In another embodiment, the invention provides a composition comprising a plasmid which includes one or more transcription cassettes for viral segment production (in one embodiment for less than 8 viral segments for influenza A and B viruses or less than 7 for influenza C viruses and in another embodiment at least one modified segment where there are at least two segments, where the modified segment is modified so that a functional influenza protein(s) is/are not expressed from that modified segment) and one or more transcription cassettes for mRNA production. The cassettes are selected from a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a PolI promoter operably linked to an influenza virus M cDNA, e.g., a full-length influenza virus M cDNA, influenza virus linked to a PolI transcription termination sequence, and a transcription cassette comprising a PolI promoter operably linked to an influenza virus NS cDNA, e.g., a full-length influenza virus NS cDNA, linked to a PolI transcription termination sequence; and one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA. In one embodiment, the HA in a transcription cassette is a type A HA. In another embodiment, the HA in a transcription cassette is a type B HA. In one embodiment, the RNA PolI promoter is a human RNA PolI promoter. In one embodiment, the composition further includes a transcription cassette comprising a PolI promoter operably linked to an influenza virus M cDNA, e.g., one having M1 and BM2, linked to a PolI transcription termination sequence.

Further provided is a composition comprising a vector which includes a transcription cassette comprising a PolI promoter and a PolI transcription termination sequence and a PolII promoter and a PolI transcription termination sequence each operably linked to a cDNA for influenza virus PA, e.g., a full-length influenza virus PA, a transcription cassette comprising a PolI promoter and a PolI transcription termination sequence and a PolII promoter and PolII transcription termination sequence each operably linked to a cDNA for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a cDNA for influenza virus PB2, e.g., a full-length influenza virus PB2 cDNA, and a transcription cassette comprising a PolI promoter and a PolI transcription termination sequence and a PolII promoter and a PolII transcription termination sequence each operably linked to a cDNA for influenza virus NP, e.g., a full-length influenza virus NP cDNA.

The compositions of the invention may include vectors with influenza virus sequences having one or more additional mutations including additional attenuating mutations. For example, additional attenuating mutations may be desirable for some recombinant human influenza viruses employed in vaccines, e.g., for H5 viruses including $HA_{Av}$ viruses. For example, additional mutations may include, but are not limited to, a substitution in the HA cleavage site, a substitution in or a deletion in the transmembrane (TM) domain of M2 (see U.S. Pat. No. 6,872,395 and U.S. application Ser. No. 60/944,680), e.g., for influenza A virus, substitutions may be at any one or more of residues 25 to 43 in the TM domain of M2, for instance, at positions 27, 30, 31, 34, 38, and/or 41 of the TM domain of M2 (for example, a V27T, A30P, S31N, or W41A substitution), or a deletion in the TM domain of M2, for instance, a deletion of at least residue 29, 30 or 31, or any combination thereof, in the TM domain of M2, a deletion in the cytoplasmic tail of M2, e.g., including a deletion of 2 or more residues and up to 21 residues of the cytoplasmic tail of M2, such as a deletion of the 11 C-terminal amino acids of the M2 cytoplasmic tail, or one or more substitutions associated with temperature sensitivity (e.g., cold adapted viruses), such as substitutions in PB1, e.g., K391E, E581G, or A661T, substitutions in PB2, e.g., N265S, and/or substitutions in NP, e.g., D34G (see Jin et al., *Virology*, 30:18 (2003)).

Exemplary Methods

The invention also provides a method to prepare an influenza virus. The method includes contacting a cell with at least two VLPs, each VLP having one and up to eight segments selected from an influenza virus PA segment; an influenza virus PB1 segment; an influenza virus PB2 segment; an influenza virus NP segment; an influenza virus M segment; an influenza virus NS segment; an influenza virus NA segment; or an influenza virus HA segment; and wherein the VLP comprises PA, PB1, PB2, NP, and HA or a non-influenza virus host cell binding protein, and NA; wherein in one embodiment, the first VLP has at least one segment that is not present in the second VLP and the second VLP has at least one viral segment that is not present in the first host cell. The HA segment may be any one of H1-H18 and the NA may be any one of N1-N11.

Each VLP may be prepared by contacting a cell with one or up to eight transcription cassettes for viral segment production selected from a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, and/or a transcription cassette comprising a PolI promoter operably linked to an influenza virus M cDNA, e.g., a full-length influenza virus M cDNA, linked to a PolI transcription termination sequence and/or a transcription cassette comprising a PolI promoter operably linked to an influenza virus NS cDNA, e.g., a full-length influenza virus NS cDNA, linked to a PolI transcription termination sequence; and a plasmid which includes one or more transcription cassettes selected from a transcription cassette, a transcription cassette comprising a PolII promoter operably linked to a DNA coding region for influenza virus PA, a transcription cassette comprising a PolII promoter operably linked to a DNA coding region for influenza virus PB1, a transcription cassette comprising a PolII promoter operably linked to a DNA coding region for influenza virus PB2, and/or a transcription cassette comprising a PolII promoter operably linked to a DNA coding region for influenza virus NP.

In one embodiment, a method to prepare a VLP includes contacting a cell with a vector which includes one and up to eight transcription cassettes for vRNA production selected from a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NA cDNA, e.g., a full-length influenza virus NA cDNA, linked to a PolI transcription termination sequence, a transcription cassette comprising a promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, and optionally includes one or more transcription cassettes selected from a transcription cassette comprising a PolI promoter and a PolI transcription termination sequence and a PolII promoter and a PolII transcription termination sequence each operably linked to a cDNA for influenza virus PA, e.g., a full-length influenza virus PA cDNA, a transcription cassette comprising a PolI promoter and a PolI transcription termination sequence and a PolII promoter and a PolII transcription termination sequence each operably linked to a cDNA for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a cDNA for influenza virus PB2, e.g., a full-length influenza virus PB2 cDNA, and/or a transcription cassette comprising a PolI promoter and a PolI transcription termination sequence and a PolII promoter and a PolII transcription termination sequence each operably linked to a cDNA for influenza virus NP e.g., a full-length influenza virus NP cDNA.

In one embodiment, the method of the invention includes contacting a cell with one or more vectors comprising a transcription cassette comprising a promoter linked to 5' influenza virus sequences comprising 5' influenza virus noncoding sequences and optionally adjacent portions of the coding sequence (see PCT/US03/04233, which is incorporated by reference herein), linked to a DNA of interest linked to 3' influenza virus sequences comprising 3' influenza virus noncoding sequences and optionally adjacent portions of the coding sequence, linked to a transcription termination sequence (see PCT/US03/04233). In one embodiment, the DNA of interest is in the sense orientation. In another embodiment, the DNA of interest is in the negative sense orientation. The DNA of interest may include an open reading frame encoding an immunogenic polypeptide or peptide of a pathogen or a therapeutic polypeptide or peptide. The DNA of interest may be operably linked to a PolI promoter and a PolI transcription termination sequence, and/or the DNA of interest is operably linked to a PolII promoter and a PolII transcription termination sequence.

The methods of the invention may be employed to prepare recombinant influenza viruses. In one embodiment, the methods include the use of vectors with influenza virus sequences having mutations including additional attenuating mutations. For example, attenuating mutations may be desirable for some recombinant human influenza viruses employed in vaccines, e.g., for H5 viruses including $HA_{Av}$ viruses. For example, additional mutations may include, but are not limited to, a substitution in the HA cleavage site, a substitution in or a deletion in the transmembrane (TM) domain of M2 (see U.S. Pat. No. 6,872,395 and U.S. application Ser. No. 60/944,680), e.g., for influenza A virus, substitutions may be at any one or more of residues 25 to 43 in the TM domain of M2, for instance, at positions 27, 30, 31, 34, 38, and/or 41 of the TM domain of M2 (for example, a V27T, A30P, S31N, or W41A substitution), or a deletion in the TM domain of M2, for instance, a deletion of at least residue 29, 30 or 31, or any combination thereof, in the TM domain of M2, a deletion in the cytoplasmic tail of M2, e.g., including a deletion of 2 or more residues and up to 21 residues of the cytoplasmic tail of M2, such as a deletion of the 11 C-terminal amino acids of the M2 cytoplasmic tail, or one or more substitutions associated with temperature sensitivity (e.g., cold adapted viruses), such as substitutions in PB1, e.g., K391E, E581G, or A661T, substitutions in PB2, e.g., N265S, and/or substitutions in NP, e.g., D34G (see Jin et al., *Virology,* 306:18 (2003)).

Cell Lines and Influenza Viruses that can be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

In one embodiment, the cells are WHO certified, or certifiable, continuous cell lines, e.g., Vero cells. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The vaccine virus may be purified by a process that has been shown to give consistent results (see, e.g., World Health Organization, 1982).

In one embodiment, a complete characterization of the cell lines to be used is established, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Exemplary cells for propagating or producing influenza virus include but are not limited to 293 cells, a 293T cells, DF-1 cells, A549 cells, Vero cells or MDCK cells.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Webster et al., 1977); or a nonionic detergent such as that commercialized under the name TRITON X100. The hemagglutinin may also be isolated after treatment of the virions with a protease such as bromelin, then purified by a method.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines of the invention are provided by inactivating replicated virus of the invention using known methods, such as, but not limited to, formalin or 1-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens may be employed.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; *Avery's Drug Treatment*, 1987. The composition of the invention is generally presented in the form of individual doses (unit doses).

Conventional vaccines generally contain about 0.1 to 200 µg, e.g., 10 to 15 µg, of HA from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Avery's, 1987.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided.

Heterogeneity in a vaccine may be provided by mixing replicated influenza viruses for at least two influenza virus strains, such as 2-50 strains or any range or value therein. Influenza A or B virus strains having a modern antigenic composition may be employed. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-$\alpha$, interferon-$\beta$, interferon-$\gamma$, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. The gene therapy compositions of the invention may be provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Avery, 1987. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. One mode of using a pharmaceutical composition of the present invention is by intramuscular or subcutaneous application. See, e.g., Avery, 1987.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent suggested dose ranges. However, the dosage will be tailored to the individual subject, as is understood and determinable by one of skill in the art. See, e.g., Avery's, 1987; and Ebadi, 1985.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Health Service (PHS), which is usually 15 µg, per component for older children<3 years of age, and 7.5 µg per component for older children<3 years of age. The quantity of NA can also be standardized, however, this glycoprotein can be labile during the processor purification and storage. Each 0.5-ml dose of vaccine may contain approximately 1-50 billion virus particles, e.g., 10 billion particles.

Example I

Characterization of a 7 Segment Influenza A Virus

NA-deficient viruses that lack the NA vRNA combine several attractive features: (i) high levels of attenuation; (ii) ease of generation by reverse genetics and (ii) biosafety, since there are no point mutations that may cause reversion to the wild-type phenotype. Moreover, reassortment of the 7 segment virus with a circulating wild-type strain would only re-create the wild-type strain from which the 7 segment virus was derived. Such a virus may be of particular interest for H5 and H3 influenza viruses. Although several candidate H5N1 virus vaccines have been developed (Bresson et al., 2006; Treanor et al., 2006), preclinical and clinical studies with inactivated subvirion or split vaccines have demonstrated that high doses of HA are needed to achieve adequate immune responses (Treanor et al., 2006). Even in the presence of adjuvant, 30 µg of HA were required to achieve an immune response equivalent to that typically found for non-adjuvanted H3 HA vaccines (Bresson et al., 2006).

Previously, viruses that lacked NA activity were prepared by passaging virus in the presence of an antibody to the NA molecule, while sialidase activity was provided by a cell line expressing NA or by exogenously applied bacterial sialidase. Both approaches resulted in viruses that contained large internal deletions in their NA genes. These viruses, which have an internally deleted NA segment and do not express functional NA (they are NA-deficient viruses), replicated in cell culture, eggs, and mice. Viruses deficient in NA may also be passaged in mutant cells such as those disclosed in U.S. application Ser. No. 10/081,170, e.g., MaKS cells, the disclosure of which is incorporated by reference herein, and Brandi et al., *J. Biol. Chem.*, 263: 16283 (1988)).

Materials and Methods

Viruses.

Human H5N1 viruses [A/Vietnam/1203/2004 (VN1203) and A/Vietnam/1194/2004 (VN1204)] were used. Human isolates were grown in Madin-Darby canine kidney (MDCK) cells and maintained in minimal essential medium with 5% newborn calf serum. All experiments with live viruses and with transfectants generated by reverse genetics were performed in a biosafety level 3 containment laboratory approved for such use by the CDC and the U.S. Department of Agriculture.

Plasmid Construction and Reverse Genetics.

The cDNAs of the VN1194 and another human H5N1 virus A/Indonesia/7/2005 (Indonesia7) were synthesized by reverse transcription of viral RNA with an oligonucleotide (Uni 12) complementary to the conserved 3' end of the viral RNA, as described in Hatta et al. (2001). The cDNA was amplified by PCR with gene-specific oligonucleotide primers and then sequenced. The generation of plasmid constructs for viral RNA production (pPolI), and containing the genes of VN1194 and Indonesia7 viruses flanked by the human RNA polymerase I promoter and the mouse RNA polymerase I terminator, is described in Neumann et al. (1999). All constructs were sequenced to ensure the absence of unwanted mutations. Automated sequencing was performed at the University of Wisconsin-Madison Biotechnology Center. Transfectant viruses were produced by reverse genetics as described by Neumann et al. (1999).

Experimental Infection.

The $MLD_{50}$, that is, the dose of virus lethal to 50% of mice, for the VN1194 and VN1194NA- viruses (a 7 segment virus lacking the NA vRNA) was determined by intranasal inoculation of anesthetized 4-week-old female BALB/c mice with 10-fold serial dilutions of virus. Infected mice were observed daily for 14 days. For virus titration in organs, mice were infected intranasally with 100 (VN1194) or $10^5$ PFU (VN1194NA-) of virus and euthanized on day 3 and day 6 post-infection as described in Gao et al. (1999).

To evaluate the protective efficacy of VN1194NA- against challenge with lethal doses of highly pathogenic H5N1 viruses, each mouse was infected intranasally with $10^5$ PFU of VN1194NA-. As a control, mice were inoculated intranasally with phosphate-buffered saline (PBS). Fourteen days later, serum samples, as well as trachea-lung and nasal washes, were collected from a subset of mice and examined for virus-specific immunoglobulin A (IgA) or G (IgG) antibodies, using VN1194 as an antigen, by use of an enzyme-linked immunosorbent assay (ELISA). On day 21 post-vaccination, the remaining mice were challenged intranasally with 100 $MLD_{50}$ of wild-type VN1194, VN1203, or Indonesia7 virus and monitored daily for survival and body weight for 14 days. Virus titers were determined in organs from six mice per group at 3 and 6 days post-challenge.

Results

A mutant A/Vietnam/1194/04 (H5N1) virus lacking the NA segment ("VN1194NA-") and a virus in which the NA segment was replaced with a mutant NA segment possessing an eGFP gene ("VN1194NAeGFP") were found to replicate in MDCK cells without exogenous neuraminidase treatment (Table 1).

TABLE 1

| Virus titers in MDCK cells |
|---|
| VN1194NA-P2 virus: 8.5 × $10^5$ pfu/ml |
| VN1194NA-P10 virus: 4.3 × $10^6$ pfu/ml |
| VN1194NAeGFP P2 virus: 2.3 × $10^4$ pfu/ml |
| VN1194NAeGFP P10 virus: 3.0 × $10^4$ pfu/ml |

The resulting viruses were characterized for the presence or absence of NA, eGFP or NS segments. The $MLD_{50}$ for the VN1194NA⁻ virus in mice was >$10^5$ (P10: 4.3×$10^6$ pfu/ml) while that for wild-type virus was 3.1. Wild type VN1194 virus was isolated from a variety of organs, including brain. VN1194NA- was isolated only from nasal turbinates, indicating that the VN1194NA- virus is attenuated in mice.

To test the NA virus as a vaccine, Balb/c (4 week old, female) mice were immunized with VN1194NA- virus. Challenge viruses were VN1194 wild-type, A/Vietnam/1203/04, and A/Indonesia/7/05 (100 $LD_{50}$). The vaccination schedule was as follows, day 0, vaccination; days 3 and 6, organ sampling from 3 mice/group; day 14, serum, lung and NT wash collection (5 mice/group); day 21, challenge; days 24 and 27, organ sampling, 6 mice/group; from day 21 to day 35, weigh and morbidity check, 8 mice/group daily; and day 35, end.

All of the mice vaccinated with VN1194NA- survived a lethal challenge (100 $LD_{50}$) with highly pathogenic H5N1 viruses [wild type VN1194, A/Vietnam/1203/04 (Clade 1; VN1203), and A/Indonesia/7/05 (Clade 2; Indonesia7)], whereas all of the control mice died or had to be euthanized due to their disease by day 8 post-challenge. High titers of IgG and IgA antibodies against wild-type VN1194 were detected in the serum, lung and nasal washes of vaccinated mice 14 days after immunization. Although the body weight of the vaccinated mice challenged with VN1194 and VN1203 virus dropped slightly on day 4 post-challenge, the mice recovered. Similarly, the body weight of vaccinated mice challenged with Indonesia7 dropped until day 6 post-challenge; however, all of the mice again recovered completely. By contrast, the control mice did not recover. Viruses were isolated from a variety of organs in control mice, whereas virus replication was restricted to respiratory organs in vaccinated mice.

Summary

An A/Vietnam/1194/04(H5N1) (VN1194) mutant virus was generated that entirely lacks an NA gene (VN1194NA-), that is, it contains only seven RNA segments. In MDCK cells, this virus grew to about $10^2$ plaque-forming units (pfu) per ml of cell culture supernatant. However, after 10 consecutive passages in MDCK cells, virus titers increased to about $10^6$ pfu per ml of cell culture supernatant, suggesting that VN1194NA- had acquired mutations that allowed its efficient growth in cell culture. Nevertheless, this variant remained highly attenuated in mice, with an $MLD_{50}$ (the amount of viruses required to kill 50% of infected animals) of >$10^5$ pfu. By contrast, the $MLD_{50}$ for the parental VN1194 virus was 3.1 pfu. Hence, the 7 segment virus grows to reasonable titers in cell culture but is highly attenuated in mice, suggesting its potential for use as a live attenuated vaccine.

A NA- VLP may be employed with a complementing VLP, such as those described in Example III and in the claims, to infect a cell and produce replication competent influenza virus Example II 7 Segment Influenza Viruses and Additional Attenuating Mutations To establish NA-deficient influenza viruses as live, attenuated vaccines, recombinant viruses of the NA-deficient influenza virus H3 and H5 subtypes are generated and evaluated. Live, attenuated, NA-deficient H3 vaccine viruses may provide protection against 'seasonal influenza'. By contrast, live, attenuated, NA-deficient H5 vaccine viruses likely are reserved for a pandemic caused by a virus of this subtype, since the use of this vaccine may introduce a new HA subtype into human populations. In the event of an H5N1 influenza virus pandemic, when viruses of this subtype are already circulating in humans, a live, attenuated H5N1 vaccine would be invaluable, as its immunogenicity would be expected to be superior to that of inactivated vaccines.

Generation of a Live, Attenuated. NA-Deficient H5N1 Virus

Highly pathogenic H5N1 influenza viruses now fall into multiple clades, prompting the generation of candidate vaccine viruses for two of these clades: NA-deficient A/Vietnam/1194/04 (VN1194, clade 1) and A/Indonesia/5/05 (Ind/05, clade 2).

To generate a NA-deficient VN1194 virus for use as a vaccine, a RNA polymerase I based plasmid for the expression of a modified HA protein encoding an avirulent-type HA cleavage site sequence is prepared. The HA protein of VN1194 HA contains a multibasic cleavage site as shown in Table 2 (cleavage occurs between the Arg and Gly residues as depicted by the arrow).

TABLE 2

| | | | | | | | | | ↓ | |
|---|---|---|---|---|---|---|---|---|---|---|
| VN1194 | R | E | R | R | R | K | K | R | | G |
| | AGA | GAG | AGA | AGA | AGA | AAA | AAG | AGA | | GGA |
| VN1194-HA$_{Av}$ | | | | | R | E | T | R | | G |
| | | | | | AGA | GAA | ACG | AGA | | GGA |

To generate an avirulent-type HA cleavage sequence, the multibasic sequence is altered to RETR, an avirulent-type sequence. The conversion of the HA cleavage site from a 'virulent' to an 'avirulent' type further attenuates the 7 segment vaccine virus. Other attenuating mutations useful for vaccine viruses such as H5 and H3 viruses are disclosed in Example III.

To generate an NA-deficient Ind/05 virus, vRNA is isolated, reverse transcribed, cloned, and sequenced. To establish a consensus sequence for this virus, at least three clones per segment are sequenced. Full-length viral cDNAs that adhere to the consensus sequence are cloned between RNA polymerase I promoter and terminator sequences as described in Hatta et al. (2001) and Neumann et al. (1999). A RNA polymerase I plasmid expressing a 'detoxified' HA protein of Ind/05 is also prepared.

Vero cells that are qualified for human vaccine virus production are used to generate virus. Vero cells suitable for this purpose can be obtained from ATCC. Specifically, Vero cells are transfected with 7 RNA polymerase I plasmids for the synthesis of VN1194 or Ind/05 vRNAs (encoding wild-type PB2, PB1, PA, NP, M, and NS segments, and the modified HA segment; no NA segment plasmid is included), and with 4 plasmids for the expression of the nucleoprotein and the three polymerase proteins. When a cytopathic effect (CPE) is observed, virus-containing cell culture supernatants are harvested and all 7 vRNA segments are sequenced to confirm the authenticity of the viruses (VN1194HA$_{Av}$NA- or Ind/05HA$_{Av}$NA-, respectively). Since the initial titers of VN1194HA$_{Av}$NA- and Ind/05HA$_{Av}$NA- may be low, a CPE may not initially be observed in plasmid-transfected cells. In this event, cell culture supernatant from plasmid-transfected Vero cells is collected at 96 hours post-infection and passaged once in fresh Vero cells. Once a CPE is observed, the supernatants are collected and the authenticity of the viruses tested. For the original VN1194HA$_{Av}$NA- and Ind/05HA$_{Av}$NA- virus stocks, their titers are determined by plaque assays in MDCK cells.

To obtain variants that grow to reasonable titers in cell culture, the virus is serially passaged, in parallel, in both Vero and MDCK cells. Briefly, cells are infected at a multiplicity of infection (m.o.i.) of 0.01 and virus-containing cell culture supernatants harvested when most of the cells have lysed due to virus infection. After each passage, virus titers are determined in MDCK cells. Viruses are passaged until titers reach at least $10^6$ pfu per ml of cell culture supernatant, e.g., about 8 to 12 serial passages. The variant (i.e., Vero or MDCK grown virus) that grows to the highest titers is used.

Once VN1194HA$_{Av}$NA- and Ind/05HA$_{Av}$NA- variants that grow to high titers in cell culture are obtained, stock viruses are generated, aliquoted, and stored at −80° C. Stock viruses are sequenced entirely to confirm their authenticity and to identify the mutations that arose from adaptation to Vero or MDCK cells.

In parallel, both wild-type viruses (i.e., VN1194 and Ind/05) are generated in Vero cells. These viruses are used in both live and formalin-inactivated forms as controls. For formalin-inactivated vaccines, the HA concentration is established as described in Katz et al. (1989).

Generation of an NA-Deficient H3 Virus

Following the strategy outlined above for the generation of NA-deficient H5 viruses, a NA-deficient H3 virus is generated for use against 'seasonal influenza'. Specifically, a NA-deficient virus based on the A/Yokohama/2017/03 (Yok) virus, a recent human H3N2 virus, is prepared using reverse genetics. A Yok virus that lacks the NA segment (YokNA-) is generated and high-growth variants are prepared in Vero and MDCK cells. The high-growth YokNA- variant may be developed into a master seed virus. High-growth YokNA- variants developed in Vero and MDCK cells are sequenced completely, and all mutations found in the high-growth, Vero cell grown YokNA- variant are introduced into RNA polymerase I plasmids for YokNA-generation, using site-directed mutagenesis. All mutations found in the high-growth, MDCK cell grown YokNA- variant are introduced into another set of RNA polymerase I plasmids for YokNA- generation, using site-directed mutagenesis.

As described above for H5N1 viruses, the wild-type Yok virus is also generated in Vero cells. Both live and formalin-inactivated Yok viruses serve as controls. For formalin-inactivated vaccines, the HA concentration is established.

If high-growth variants are not obtained after 15 serial passages, cell lines that produce reduced amounts of sialic acids (hence alleviating the need for NA activity) are used to support the growth of viruses that lack NA, e.g., a MDCK cell line that expresses low amounts of sialic acid (Hughes et al., 2001) and supports efficient growth of an NA-deficient virus (Shinya et al., 2004). A similar strategy may be used to establish a Vero cell line that expresses low amounts of sialic acid.

Pathogenicity and Immunogenicity of NA-Deficient H5 and H3 Influenza Viruses

Live, attenuated vaccines are sufficiently attenuated (cause no or mild disease symptoms), immunogenic (stimulate strong humoral and cellular immune responses), and protective (provide protective immunity to immunized individuals).

The following viruses are assessed for pathogenicity and immunogenicity:

TABLE 3

| H5N1 viruses | |
|---|---|
| VN1194H$_{Av}$NA- | Live, attenuated, NA-deficient virus; avirulent HA cleavage sequence |
| VN1194 | Parental virus, live |
| VN1194$_{Inact.}$ | Parental virus, formalin-inactivated |

TABLE 3-continued

| | |
|---|---|
| Ind/05HA$_{Av}$NA- | Live, attenuated, NA-deficient virus; avirulent HA cleavage sequence |
| Ind/05 | Parental virus, live |
| Ind/05$_{Inact.}$ | Parental virus, formalin-inactivated |
| H3N2 virus | |
| YokNA- | Live, attenuated, NA-deficient virus |
| Yak | Parental virus, live |
| Yok$_{Inact.}$ | Parental virus, formalin-inactivated |

Pathogenicity and Virulence of NA-Deficient H5 Viruses (VN1194HA$_{Av}$NA-, Ind/05HA$_{Av}$NA-)

Highly pathogenic H5N1 influenza viruses, such as VN1194 and Ind/05, typically kill mice within 8 days of infection. To assess the level of attenuation for VN1194HA$_{Av}$NA- and Ind/05HA$_{Av}$NA-, their LD$_{50}$ values are determined. LD$_{50}$ values are also determined for the parental VN1194 and Ind/05 viruses, but not for formalin-inactivated viruses.

Briefly, BALB/c mice (5 animals/group) and/or ferrets (3 animals/group) are inoculated intranasally with ten-fold dilutions of live, attenuated (VN1194HA$_{Av}$NA- and Ind/05HA$_{Av}$NA-) or live parental virus (starting from $10^5$ pfu) and observed daily for signs of disease. Control animals are inoculated with the same amount of live parental virus. Additional controls are mock-infected. Since highly pathogenic H5N1 influenza viruses are known to cause systemic infection, viral titers are determined in lungs, nasal turbinates, heart, spleen, kidney, liver, colon, pancreas, and brain on days 3 and 6 post-infection. VN1194HA$_{Av}$NA- and Ind/05HA$_{Av}$NA- virus, by contrast, show significant attenuation, that is, no virus spread beyond the respiratory organs and lower overall virus titers.

Pathogenicity and Virulence of an NA-Deficient H3 Virus (YokNA-)

In contrast to highly pathogenic H5N1 influenza viruses, human H3N2 viruses typically do not cause systemic infection in mice or ferrets and do not kill these animals. To establish the level of attenuation for YokNA- as compared to the parental Yok virus, mice and ferrets are infected intranasally as described above. Animals are observed daily for signs of disease such as weight loss, reduced activity, or sneezing (for ferrets). In parallel, virus titers are determined in nasal turbinates and lungs of infected animals on days 1, 3, and 6 post-infection. For Yok virus, signs of mild disease occur early in the infection, which may clear by day 6 post-infection. For YokNA- virus, low virus titers are observed on day 1 (reflecting the virus's limited ability to replicate) and less pronounced, if not no disease symptoms and little if any virus replication, are observed on day 3 post-infection Immunogenicity of NA-Deficient H5 and H3 Influenza Viruses For live, attenuated vaccines, the balance between attenuation and immunogenicity is important. To assess the immunogenicity of VN1194HA$_{Av}$NA-, Ind/05HA$_{Av}$NA-, and YokNA-, humoral and cellular immune responses are tested in mice, and a humoral response is tested in ferrets.

Hemagglutination Inhibition (HI) and Neutralization Tests.

To determine the levels of serum antibodies to HA, hemagglutination inhibition and neutralization tests are performed. Mice and ferrets are infected with ten-fold dilutions (starting with $10^5$ pfu) of VN1194HA$_{Av}$NA-, Ind/05HA$_{Av}$NA-, or YokNA virus. In parallel, control animals are infected with the same amounts of live parental virus or with 30 μg of HA for inactivated parental viruses. Mock-infected animals serve as negative controls. On days 7, 14, 30, and 90 post-infection, serum samples are collected from the suborbital capillary vein of mice (or the jugular vein of ferrets; the latter will be anesthetized for this procedure). Mice infected with live VN1194 or Ind/05 virus die within 7-8 days post-infection.

For live, attenuated and inactivated viruses, a two-dose regimen is also tested. Animals are infected as described above and then boosted with the same dose of virus 30 days later. This two-dose regimen is not conducted for live parental viruses, since mice infected with high doses die within 7-8 days of the first immunization, whereas those infected with low doses survive and develop sterile immunity (Katz et al., 2000).

For HI assays, serum samples are treated with receptor-destroying enzyme and sodium periodate, and then tested with H5 and H3 viruses. For H5 viruses, representative strains isolated since 1997 from birds and humans that cover both clades are included. For H3 viruses, representative human isolates from 2000 forward are included. HI assays are typically performed with chicken or turkey erythrocytes; however, these erythrocytes have low sensitivity for antibodies to H5 HA. Horse erythrocytes have improved sensitivity (Stephenson et al., 2004), therefore, horse erythrocytes are employed for HI assays with H5 viruses. Moreover, some human H3 viruses do not agglutinate chicken erythrocytes efficiently, but bind to guinea pig erythrocytes (Stephensen et al., 2003). For H3 viruses, HI assays are performed with guinea pig erythrocytes. The HI titer of serum is expressed as the reciprocal of the highest dilution of serum that causes the complete inhibition of 4 hemagglutination units of antigen. A fourfold increase in HI titers is considered significant; titers of 1:40 or more are believed to be protective (Porter et al., 1979).

For neutralization assays, serum samples are treated as described for HI assays, then mixed with equal volumes of homologous or heterologous virus (100 pfu each), incubated for 1 hour at room temperature, and then inoculated onto MDCK cells, following established protocols (Bridges et al., 2002). MDCK cells are infected with 100 pfu of virus in the presence of a control serum that does not react with H5N1 or H3N2 viruses. The neutralizing antibody titer is the reciprocal of the highest dilution of serum that reduces the plaque number by 50%.

Inactivated influenza vaccines produce higher serum HI titers than live, attenuated vaccine viruses (Cox et al., 2004). Thus, the serum HI titers induced by VN1194HAN-A-, Ind/05HA$_{Av}$NA-, and YokNA- may be low. It is possible that an antibody response is not detected in animals infected with NA-deficient viruses. While detectable serum antibody titers provide an indication of immunogenicity for inactivated vaccines, the lack of such titers does not necessarily exclude protective efficacy for the vaccine.

Antibody Response.

To further assess the humoral response to infection with VN1194HA$_{Av}$NA-, Ind/05HA$_{Av}$NA-, or YokNA- virus, IgA- and IgG-specific ELISAs are conducted on serum and bronchoalveolar lavage (BAL) samples from infected mice and ferrets.

Serum samples are obtained as described above. To obtain BAL fluid, animals are euthanized, catheterized, the tracheae and lungs washed with phosphate-buffered saline (PBS), and the fluid drawn into a syringe attached to the catheter. The levels of IgA and IgG antibodies are determined by use of established protocols (Kida et al., 1982). Briefly, the viruses used for immunization are absorbed to microtiter plates, incubated with serially diluted serum or BAL samples, washed, and incubated with anti-mouse peroxidase-conjugated IgA or IgG antibodies. Samples are then incubated with a peroxidase substrate. The reaction product is quantified on an ELISA reader at 405 nm. Samples derived from mock-infected animals are used to establish a baseline.

Inactivated influenza virus vaccines induce appreciably higher levels of serum antibodies than do live, attenuated vaccines (Cox et al., 2004). Yet, live, attenuated influenza virus vaccines are more potent inducers of IgA in nasal washes, while inactivated vaccines induce predominantly IgG mucosal antibodies. For animals infected with the live, attenuated, NA-deficient viruses and the live parental viruses, relatively low levels of serum antibodies are expected relative to animals infected with inactivated viruses. The live viruses, however, are expected to be superior to inactivated viruses with respect to inducing mucosal IgA antibodies.

Cellular Immune Response.

To assess the cellular immune responses to infection with live, attenuated NA-deficient H5 or H3 viruses, virus-specific CD8 T cell responses in mice are measured. Animals are inoculated with live parental virus, live, attenuated virus, or inactivated virus, as described above. On days 7, 14, 30, and 90 post-infection (for the parental H5 viruses, only the first time-point can be tested since animals die by day 7 or 8 post-infection), BAL fluids are collected as described above, as well as lungs, spleen and cervical and mediastinal lymph nodes. For lymph nodes and spleen, single cell suspensions of mononuclear cells are prepared as described in Hogan et al. (2001). For lungs, a cell suspension is generated according to established protocols (Masopust et al., 2001) and mononuclear cells obtained using a Percoll gradient. All mononuclear cells are then stained with labeled-MHC I tetramers specific to the influenza epitopes ($K^d$ $NP_{147-156}$:TYQRTRALV (SEQ ID NO: 1); $K^d$ $HA_{518-526}$: IYSTVASSL (SEQ ID NO: 2)) in BALB/c mice, and with anti-CD8, anti-LFA-1, and anti-CD62L antibodies. The number of virus-specific CD8 T cells is determined by flow cytometry.

In parallel, intracellular cytokine staining is used to measure functional cytotoxic T cells. Mononuclear cells are stimulated with epitope peptides in the presence of Brefeldin A, which inhibits cytokine secretion. Staining for cell surface CD8 and intracellular IFN-γ, TNF-α, or IL-2 is achieved with a Cytofix/Cytoperm kit (BD-Pharmingen), and the number of cytokine-producing CD8 T cells is measured by flow cytometry.

Live, attenuated influenza viruses typically elicit a stronger cellular immune response than inactivated viruses. More potent virus-specific CD8 T cell stimulation is expected in animals infected with live parental viruses or live, attenuated viruses than in animals infected with inactivated viruses.

Protective Efficacy of NA-Deficient H5N1 Viruses

To assess the protective efficacy of NA-deficient viruses, groups of mice (or ferrets; 9 animals/group) are immunized intranasally with the same doses of live, attenuated, NA-deficient viruses or inactivated viruses that were tested for immunogenicity. If the immunogenicity studies show the two-dose regimen with a booster immunization to be more efficient than a single immunization, a booster immunization is also conducted for protection studies. If both regimens are of comparable efficacy, mice are immunized only once. Mock-infected animals serve as controls. One to three months post-immunization, animals are challenged with lethal doses (10 or 100 $MLD_{50}$ for mice; $10^6$ pfu for ferrets) of homologous VN1194 or Ind/05 virus. Animals are observed daily for signs of disease. On days 3 and 6 post-challenge, three animals per group are euthanized. Virus titers in organs and serum antibody titers are determined.

For mouse experiments, mock-vaccinated animals are expected to succumb to systemic infection caused by VN1194 or Ind/05 virus. For ferret experiments, mock-vaccinated animals challenged with Ind/05 virus are expected to die, whereas those infected with VN1194 are expected to lose weight but to recover from virus infection. By contrast, all vaccinated animals are expected to be protected against lethal challenge or weight loss. The live, attenuated NA-deficient viruses are expected to provide better protection than the inactivated viruses. Better protection may include higher survival rates, lower virus titers, restricted virus spread, and/or reduced weight loss after challenge.

Vaccines to highly pathogenic H5N1 influenza viruses may provide protection against isolates from both clades. To assess whether the live, attenuated NA-deficient H5N1 vaccine viruses provide cross protection, animals are immunized as above and challenged with 10 or 100 $MLD_{50}$ (for mice), or with $10^6$ pfu (for ferrets), of the respective heterologous virus (i.e., animals immunized with $VN1194HA_{4v}NA$- (clade 1) virus are challenged with Ind/05 (clade 2) virus and vice versa). Some cross-protection is expected, although the protective efficacy may be lower than that observed with homologous virus.

Protective Efficacy of an NA-Deficient H3N2 Virus

To establish the protective efficacy of an NA-deficient H3N2 virus, immunization and challenge studies are carried out essentially as described above for H5N1 viruses. Groups of mice (and ferrets; 9 animals/group) are immunized intranasally with the same doses of YokNA- or $Yok_{Inact}$ that are tested for immunogenicity. Mock-infected animals serve as controls. One to three months post-immunization, animals are challenged with $10^6$ pfu of Yok virus. Animals are observed daily for signs of disease. On days 3 and 6 post-challenge, three animals per group are euthanized. Virus titers in nasal turbinates and lungs and serum antibody titers are determined.

Signs of disease are expected in mock-immunized control animals but not in vaccinated animals. Limited virus replication is expected in the nasal turbinates and lungs of vaccinated animals.

If $VN1194HA_{4v}NA$-, $Ind/05HA_{4v}NA$-, and/or YokNA- are too pathogenic, additional attenuating mutations are introduced into their genomes. If the NA-deficient viruses are too attenuated, viruses that contain all 8 vRNAs but lack functional NA, for example, by deleting large portions of the NA reading frame are generated.

The invention will be further described by the following non-limiting examples.

Example III

Reverse genetics systems for influenza A viruses are built on the concept that cells are transfected with plasmids for the synthesis of all eight influenza A viral genomic segments within one cell. A different strategy for the generation of influenza viruses from plasmids is provided herein. Cells are transfected with seven RNA polymerase I plasmids (for example, the plasmid encoding the HA vRNA is omitted). Cells are cotransfected with plasmids expressing the polymerase and NP proteins to initiate viral replication and transcription. The HA protein is provided from a protein expression plasmid or from a stable cell line. Virus-like particles (VLPs) are released that possess only seven vRNA segments. These particles can infect fresh cells, but will not undergo additional rounds of propagation due to the lack of the HA vRNA.

In parallel, cells are transfected with a different set of seven RNA polymerase I plasmids (any segment except that lacking in the parallel experiment can be omitted; in the example described here, any segment except HA can be omitted). The ‘missing’ protein is provided from a protein expressing plasmid or cell line; cells are also transfected with proteins expression plasmids for the polymerases and NP. As described above, VLPs possessing seven vRNAs are released.

The two populations of VLPs (one lacking the HA viral RNA; the other lacking one of the other seven viral RNAs) are mixed and inoculated into fresh cells. In cells infected with both types of VLPs, all eight vRNAs will be present and infectious influenza viruses will be generated.

Similarly, infectious influenza viruses can be generated from VLPs possessing fewer than seven viral RNAs. Any combination of VLPs can be used as long as all eight different vRNAs are present in VLP-infected cells: for example, eight different VLPs could be generated that possess one vRNA each. If a cell is infected with VLPs possessing the PB2, PB1, PA, HA, NP, NA, M, or NS viral RNAs separately, infectious virus will be generated. In another example, one population of VLPs could possess four viral RNAs, and a second population of VLPs could possess the remaining four viral RNAs. Again, co-infection of cells with these two populations of VLPs results in the generation of replicating virus.

Procedure

1. Generation of VLPs (lacking the PB2 or HA vRNA segment, respectively) in 293T cells.

TABLE 4

| | pPolI plasmids | | | Protein |
|---|---|---|---|---|
| | pPolI-PB2 | pPolI-HA | Remaining six segments | expression plasmids |
| VLP-1 | — | WSN | WSN | 10 |
| VLP-2 | PR8 | — | WSN | 10 |

2. Co-infection of MDCK cells with mixed VLPs. As controls, MDCK cells were infected with VLP-1 or VLP-2 only.
3. Perform plaque assays and sequence replicating virus.

Results

Infectious virus (>$10^8$ pfu/mL) was detected in MDCK cells co-infected with VLP-1 and VLP-2, but not in MDCK cells infected with either VLP.

Sequence analysis of a plaque derived from MDCK cells co-infected with VLP-1 and -2 confirmed that the PB2 gene originated from PR8 virus, and that the HA gene originated from WSN virus.

Conclusion

Infectious virus can be generated upon co-infection of cells with two seven-segment viruses lacking different vRNAs.

This is a new method for producing infectious replication-competent influenza viruses/vaccines from cDNAs, which can be designed to incorporate any HA/NA combination corresponding to seasonal/pandemic influenza, as well as various attenuating, stabilizing, or growth-enhancing mutations, and/or the introduction of heterologous sequences, and a host of other innovations related to the study of influenza and the production of vaccines.

Example IV

Experiment 1

Two VLPs possessing different sets of seven viral RNAs (vRNAs) were generated. Specifically, 293T cells were transfected with plasmids expressing all viral proteins, and with plasmids expressing seven vRNAs:

a. In VLP-1, the PB2-vRNA was omitted
b. In VLP-2, the HA-vRNA was omitted.

TABLE 5

| | pPolI plasmids | | | Protein expression |
|---|---|---|---|---|
| | pPolI-PB2 | pPolI-HA | Other 6 | plasmids |
| VLP-1 | — | WSN | WSN | 10 |
| VLP-2 | PR8 | — | WSN | 10 |

The VLP-containing supernatants of plasmid-transfected cells were collected and mixed. The VLP mixture was used to infect MDCK cells. As controls, MDCK cells were infected with VLP-1 or VLP-2 only. High titers ($3\times10^8$ PFU/mL) of replicating virus were detected in MDCK cells infected with both VLPs. Sequence analysis confirmed that the replicating virus possessed the HA segment of WSN virus and the PB2 segment of PR8 virus. Replicating virus was not detected in MDCK cells infected with one VLP only.

Thus, infectious influenza viruses can be generated from two replication-incompetent VLPs.

Experiment 2

Two VLPs possessing different sets of four vRNAs were generated. VLP-4 possessed the PB1, PB2, PA, and HA vRNAs and VLP-3 possessed the NP, NA, M, and NS vRNAs. The experiment was carried out as described above.

In MDCK cells co-infected with VLP-3 and VLP-4, a high virus titer ($1.8\times10^8$ PFU/mL) was detected. Therefore, infectious influenza viruses can be generated from two replication-incompetent VLPs possessing four vRNAs each.

TABLE 6

| | pPolI plasmids | | |
|---|---|---|---|
| | pPolI-PB2 pPolI-PB1 pPolI-PA pPolI-HA | pPolI-NP pPolI-NA pPolI-M pPolI-NS | Protein expression plasmids |
| VLP-3 | — | WSN | 10 |
| VLP-4 | WSN | — | 10 |

Experiment 3

Eight VLPs possessing one vRNA each were generated (see Table 7). The experiment was carried out as described above. No cytopathic effect or hemagglutination titer was detected in VLP-infected MDCK cells.

TABLE 7

| pPolI plasmids | | Protein expression plasmids |
|---|---|---|
| VLP-5 | pPolI-WSN-PB2 only | 10 |
| VLP-6 | pPolI-WSN-PB1 only | 10 |
| VLP-7 | pPolI-WSN-PA only | 10 |
| VLP-8 | pPolI-WSN-HA only | 10 |
| VLP-9 | pPolI-WSN-NP only | 10 |
| VLP-10 | pPolI-WSN-NA only | 10 |
| VLP-11 | pPolI-WSN-M only | 10 |
| VLP-12 | pPolI-WSN-NS only | 10 |

REFERENCES

Akarsu et al., *EMBO J.*, 22:4646 (2003).
Avery's, Drug Treatment: Principles and Practice of Clinical Pharmacology and Therapeutics, ADIS Press, Ltd., 3rd ed., Williams and Wilkins, Baltimore, Md. (1987).
Bachmeyer, 1975.
Baudin et al., *Virology*, 281:102 (2001).
Berkow et al., The Merck Manual, 15th ed., Merck & Co., Rahway, N J 1987.
Beyer et al., *Vaccine*, 20:1340 (2002).
Bosch et al., *Virology*, 95:197 (1979).
Brandi et al., *J. Biol. Chem.*, 263:16283 (1988)
Bresson et al., *Lancet*, 367:1657 (2006).
Bridges et al., *J. Infect. Dis.*, 185:1005 (2002).
Bui et al., *J. Virology*, 70:8391 (1996).
Bui et al., *J. Virology*, 74:1781 (2000).
Chen et al., *Nat. Med.*, 7:1306 (2001).
Chen et al., *Virology*, 45:416 (2006).
Compans et al., *J. Virology*, 10:795 (1972).
Couch, *Dev. Biol.* (Basel), 115:25 (2003).
Cox et al., eds. Topley & Wilson's Microbiology and Microbial Infections. London: Arnold, 2005:634-698.
Cox et al., *Scand. J. Immunol.*, 59:1 (2004).
Ebadi, Pharmacology, Little, Brown & Co., Boston, Mass. (1985).
Edwards, *J. Infect. Dis.*, 169:68 (1994).
Elton et al., *Rev. Med. Virol.*, 20:380 (2010).
Fouchier et al., *J. Virology*, 79: 2814 (2005).
Garten et al., *Trends Microbiol.*, 7:99 (1999).
Gross et al., *Ann. Intern. Med.*, 123:518 (1995).
Guo et al., *J. Gen. Virology.*, 64:177 (1983).
Hara et al., *Genes Cells*, 6:87 (2001).
Hatta et al., *Philos. Trans. R. Soc. Lond. B. Biol. Sci.*, 356:1841 (2001).
Hatta et al., *Science*, 239:1840 (2001).
He et al., et al., *Nature*, 454:1123 (2008).
Heggeness et al., *Virology*, 118:466 (1982).
Hoffmann et al., *J. Virol.*, 79:11014 (2005).
Hogan et al., *J. Immunol.*, 166:1813 (2001).
Horimoto et al., *J. Virol.*, 68:3120 (1994).
Horimoto et al., *Vaccine*, 24:3669 (2006).
Horimoto et al., *Virus Res.*, 50:35 (1997).
http://www.oie.int/downId/AVIAN%20INFLUENZA/Graph%20HPAI/graphs%20HPAI%2002_08_2006.pdf.2006.
Huarte et al., *J. Virol.*, 77:6007 (2003).
Hughes et al., *J. Virol.*, 74:5206 (2000).
Hughes et al., *J. Virol.*, 75:3766 (2001).
Iwatsuki-Horimoto et al., *J. Virology.* 78:10149 (2004).
Jennings et al., *Cell*, 34:619 (1983).
Jin et al., *J. Virol.*, 78:995 (2004).
Jin et al., *Virology*, 306:18 (2003).
Katz et al., *Biomed. Pharmacother.*, 54:178 (2000).
Katz et al., *J. Infect. Dis.*, 160:191 (1989).
Kawaoka et al., *Virology*, 139:303 (1984).
Kida et al., *Virology*, 122:38 (1982).
Kilbourne, *Bull. M2 World Health Org.*, 41:643 (1969).
Lamb et al., In: Knipe D M, Howley P M, Griffin D E, Martin M A, Lamb R A, Roizman B, Straus S E, eds. Fields Virology. Philadelphia: Lippincott Williams & Wilkins, 2001:1487-1532.
Lipatov et al., *J. Infect. Dis.*, 191:1216 (2005).
Liu et al., *J. Virol.*, 69:1099 (1995).
Ma et al., *Virology*, 282:215 (2001).
Maassab et al., *Rev. Med. Virol.*, 9:237 (1999).
Masopust et al., *Science*, 291:2413 (2001).
Massin et al., *J. Virol.*, 75:5398 (2001).
McCown and Pekosz, *J. Virology*, 79:3595 (2005).
Mizrahi, ed., *Viral Vaccines*, Wiley-Liss, NY (1990).
Murphy, *Inf. Dis. Clin. Practice*, 1:174 (1993).
Neumann et al., *EMBO J.*, 19:6751 (2000).
Neumann et al., *J. Gen. Virol.*, 83:2635 (2002).
Neumann et al., *Proc. Natl. Acad. Sci. USA*, 96:9345 (1999).
Neumann et al., *Rev. Med. Virol.*, 12:13 (2002).
Nichol et al., *Arch. Intern. Med.*, 158:1769 (1998).
Noda and Kawaoka, *J. Virology*, 75:408 (2001).
O'Neill et al., *EMBO J.*, 17:288 (1998).
Obayashi et al., *Nature*, 454:1127 (2008).
Ogra et al., *J. Infect. Dis.*, 135:499 (1977).
Osterhaus et al., *Science*, 288:1051 (2000).
Oxford and Hockley, In Animal Virus Structure, Nermut M V, Steven A C (eds). Elsevier: New York, 1987; 213-232.
Palese, In Fields Virology, $5^{th}$ edn, Knipe D M, Howley P M, Griffin D E, Lamb R A, Martin M A, Roizman B, Straus S E (eds). Lippincott Williams & Wilkins: Philadelphia, 2007; 1647-1689.
Perales et al., *J. Virol.*, 74:1307 (2000).
Potter, *Br. Med. Bull.*, 35:69 (1979).
Robertson et al., *Biologicals*, 20:213 (1992).
Robertson et al., *Giornale di Igiene e Medicina Preventiva*, 29:4 (1988).
Ruigrok and Baudin, *J. Gen. I Virology*, 76:1009 (1995).
Sanz-Ezquerro et al., *J. Virol.*, 69:2420 (1995).
Sanz-Ezquerro et al., *J. Virol.*, 70: 1905 (1996).
Scheiffele et al., *J. Biol. Chem.*, 274:2038 (1999).
Shinya et al., *J. Virol.*, 78:3083 (2004).
Shinya et al., *Virology*, 320:258 (2004).
Smith et al., *Cochrane Database Syst. Rev.*, 2006.
Stephenson et al., *J. Med. Virol.*, 70:391 (2003).
Stephenson et al., *Virus Res.*, 103:91 (2004).
Stieneke-Grober et al., *EMBO J.*, 11:2407 (1992).
Subbarao et al., *J. Virol.*, 67:7223 (1993).
Taylor, *Am. J. Public Health* Nation's Health, 39:171 (1949).
Treanor et al., *N. Enal. J. Med.*, 354:1343 (2006).
Wagner et al., *Rev. Med. Virol.*, 12:159 (2002).
Watanabe et al., *J. Virol.*, 75:5656 (2001).
Watanabe et al., *Virology*, 299:266 (2002).
Watanabe et al., *Virus Res.*, 77:31 (2001).
Webster et al., *Microbiol. Rev.*, 56:152 (1977).
Wiley et al., *Annu. Rev. Biochem.*, 56:365 (1987).
Ye et al., *J. Virology*, 73:7467 (1999).
Zamarin et al., *PLoS Pathog.*, 1:e4 (2005).
Zhang et al., *J. Virol.*, 74:4634 (2000).
Zhang et al., *Virology*, 269:325 (2000).

All publications, patents and patent applications are incorporated herein by reference. While in the foregoing specification, this invention has been described in relation to certain embodiments thereof, and many details have been set forth for purposes of illustration, it will be apparent to those

What is claimed is:

1. A set of isolated host cells, comprising:

a first host cell for producing a first VLP with at least one and up to eight influenza A or B virus segments comprising:

one or more vectors which include at least one and up to eight transcription cassettes for production of at least one and up to eight viral segments from the genome of influenza A virus selected from:

a transcription cassette comprising a promoter operably linked to an influenza virus PA DNA;

a transcription cassette comprising a promoter operably linked to an influenza virus PB1 DNA;

a transcription cassette comprising a promoter operably linked to an influenza virus PB2 DNA;

a transcription cassette comprising a promoter operably linked to an influenza virus NP DNA;

a transcription cassette comprising a promoter operably linked to an influenza virus M DNA;

a transcription cassette comprising a promoter operably linked to an influenza virus NS DNA;

a transcription cassette comprising a promoter operably linked to an influenza virus NA DNA; or a transcription cassette comprising a promoter operably linked to an influenza virus HA DNA or a non-influenza host cell binding protein DNA; or one or more vectors which include at least one and up to eight transcription cassettes for production of at least one and up to eight viral segments from the genome of influenza B virus selected from:

a transcription cassette comprising a promoter operably linked to an influenza virus PA DNA;

a transcription cassette comprising a promoter operably linked to an influenza virus PB1 DNA;

a transcription cassette comprising a promoter operably linked to an influenza virus PB2 DNA;

a transcription cassette comprising a promoter operably linked to an influenza virus NP DNA;

a transcription cassette comprising a promoter operably linked to an influenza virus M DNA;

a transcription cassette comprising a promoter operably linked to an influenza virus NS DNA;

a transcription cassette comprising a promoter operably linked to an influenza virus NA and NB DNA; or a transcription cassette comprising a promoter operably linked to an influenza virus HA DNA or a non-influenza host cell binding protein DNA;

and one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; a transcription cassette comprising a promoter operably linked to an influenza virus NP DNA; and optionally a transcription cassette comprising a promoter operably linked to an influenza virus HA or a non-influenza host cell binding protein and a second host cell for producing a second VLP with at least one and up to eight influenza A or B virus viral segments comprising:

one or more vectors which include at least one and up to eight transcription cassettes for production of at least one and up to eight viral segments from the genome of influenza A selected from:

a transcription cassette comprising a promoter operably linked to an influenza virus PA DNA;

a transcription cassette comprising a promoter operably linked to an influenza virus PB1 DNA;

a transcription cassette comprising a promoter operably linked to an influenza virus PB2 DNA;

a transcription cassette comprising a promoter operably linked to an influenza virus NP DNA;

a transcription cassette comprising a promoter operably linked to an influenza virus M DNA;
a transcription cassette comprising a promoter operably linked to an influenza virus NS DNA;
a transcription cassette comprising a promoter operably linked to an influenza virus NA DNA;
a transcription cassette comprising a promoter operably linked to an influenza virus HA DNA or a non-influenza host cell binding protein DNA; or
one or more vectors which include at least one and up to eight transcription cassettes for production of at least one and up to eight viral segments from the genome of influenza B selected from:
a transcription cassette comprising a promoter operably linked to an influenza virus PA DNA;
a transcription cassette comprising a promoter operably linked to an influenza virus PB1 DNA;
a transcription cassette comprising a promoter operably linked to an influenza virus PB2 DNA;
a transcription cassette comprising a promoter operably linked to an influenza virus NP DNA;
a transcription cassette comprising a promoter operably linked to an influenza virus M DNA;
a transcription cassette comprising a promoter operably linked to an influenza virus NS DNA;
a transcription cassette comprising a promoter operably linked to an influenza virus NA and NB DNA;
a transcription cassette comprising a promoter operably linked to an influenza virus HA DNA or a non-influenza host cell binding protein DNA;
and
one or more vectors which include transcription cassettes for mRNA production including a transcription cassette comprising a promoter operably linked to an influenza virus PA DNA; a transcription cassette comprising a promoter operably linked to an influenza virus PB1 DNA; a transcription cassette comprising a promoter operably linked to an influenza virus PB2 DNA; and a transcription cassette comprising a promoter operably linked to an influenza virus NP DNA; and optionally a transcription cassette comprising a promoter operably linked to an influenza virus HA or a non-influenza host cell binding protein,
wherein the first host cell has at least one transcription cassette for production of at least one viral segment that is not present in the second host cell or wherein the first host cell has at least one transcription cassette for production of at least one viral segment that is modified in the corresponding viral segment in the second host cell so that a functional influenza virus protein is not expressed from the corresponding segment.

2. The set of host cells of claim 1 wherein the second host cell has at least one transcription cassette for production of at least one viral segment that is not present in the first host cell.

3. The set of host cells of claim 1 wherein the first host cell has 7 of the expression cassettes for production of the viral segments or the second host cell has 7 of the expression cassettes for production of the viral segments; or wherein the first host cell has at least 2 of the expression cassettes for production of the viral segments and the second host cell has at least 6 of the expression cassettes for production of the viral segments; or wherein the first host cell has at least 3 of the expression cassettes for production of the viral segments and the second host cell has at least 5 of the expression cassettes for production of the viral segments; or wherein the first host cell has at least 4 of the expression cassettes for production of the viral segments and the second host cell has at least 4 of the expression cassettes for production of the viral segments; or wherein the first host cell has at least 5 of the expression cassettes for production of the viral segments and the second host cell has at least 3 of the expression cassettes for production of the viral segments; or wherein the first host cell has at least 6 of the expression cassettes for production of the viral segments and the second host cell has at least 2 of the expression cassettes for production of the viral segments.

4. The set of host cells of claim 1 wherein the first host cell has less than 7 of the expression cassettes for production of the viral segments or the second host cell has less than 7 of the expression cassettes for production of the viral segments.

5. The set of host cells of claim 1 wherein if the transcription cassettes for viral segments in the first and second host cells do not include all eight influenza A virus segments, the set further comprises one or more host cells that each produce a VLP with an influenza A virus segment that is not present in the first and second host cells.

6. The set of host cells of claim 1 wherein the first host cell, the second host cell or both the first and the second host cell stably expresses one or more of the transcription cassettes for mRNA production.

7. The set of host cells of claim 1 wherein the first or second host cell further comprises a transcription cassette comprising a promoter linked to 5' influenza virus sequences comprising 5' influenza virus noncoding sequences linked to a DNA of interest linked to 3' influenza virus sequences comprising 3' influenza virus noncoding sequences linked to a transcription termination sequence.

8. The set of host cells of claim 1 wherein in the first host cell if the one or more transcription cassettes for viral segments do not include a transcription cassette comprising a promoter operably linked to an influenza virus M DNA, optionally a vector for mRNA production of M1 and M2 is included, wherein if the one or more transcription cassettes for viral segments do not include a transcription cassette comprising a promoter operably linked to an influenza virus NS DNA, optionally a vector for mRNA production of NS1 and NS2 is included, and wherein if the one or more transcription cassettes for vRNA do not include a transcription cassette comprising a promoter operably linked to an influenza virus NA DNA, a vector for mRNA production of NA is included.

9. The set of host cells of claim 1 wherein the non-influenza virus host cell binding protein comprises a filovirus protein, an antibody, an alphavirus protein, a lentivirus protein, a retrovirus protein, albumin, or a rhabdovirus protein.

10. An isolated host cell which produces virus-like particles (VLPs) with at least one and up to eight influenza A or B virus segments and has one or more vectors which include at least one and up to eight transcription cassettes for production of at least one and up to eight viral segments from the genome of influenza A virus selected from:
a transcription cassette comprising a promoter operably linked to an influenza virus PA DNA;
a transcription cassette comprising a promoter operably linked to an influenza virus PB1 DNA;
a transcription cassette comprising a promoter operably linked to an influenza virus PB2 DNA;
a transcription cassette comprising a promoter operably linked to an influenza virus NP DNA;
a transcription cassette comprising a promoter operably linked to an influenza virus M DNA;

a transcription cassette comprising a promoter operably linked to an influenza virus NS DNA;
a transcription cassette comprising a promoter operably linked to an influenza virus NA DNA; or
a transcription cassette comprising a promoter operably linked to an influenza virus HA DNA or a non-influenza host cell binding protein DNA; or
has one or more vectors which include at least one and up to eight transcription cassettes for production of at least one and up to eight viral segments from the genome of influenza B virus selected from:
a transcription cassette comprising a promoter operably linked to an influenza virus PA DNA;
a transcription cassette comprising a promoter operably linked to an influenza virus PB1 DNA;
a transcription cassette comprising a promoter operably linked to an influenza virus PB2 DNA;
a transcription cassette comprising a promoter operably linked to an influenza virus NP DNA;
a transcription cassette comprising a promoter operably linked to an influenza virus M DNA;
a transcription cassette comprising a promoter operably linked to an influenza virus NS DNA;
a transcription cassette comprising a promoter operably linked to an influenza virus NA and NB DNA; o a transcription cassette comprising a promoter operably linked to an influenza virus HA DNA or a non-influenza host cell binding protein DNA;
and one or more vectors which include transcription cassettes for mRNA production including a transcription cassette comprising a promoter operably linked to an influenza virus PA DNA; a transcription cassette comprising a promoter operably linked to an influenza virus PB1 DNA: a transcription cassette comprising a promoter operably linked to an influenza virus PB2 DNA; a transcription cassette comprising a promoter operably linked to an influenza virus NP DNA; and optionally a transcription cassette comprising a promoter operably linked to an influenza virus HA or a non-influenza host cell binding protein DNA,
wherein if the host cell has a transcription cassette for only one viral segment, the segment encodes a functional influenza virus protein, wherein if the host cell has a transcription cassette for seven viral segments, the host cell does not include sequences corresponding to NA coding or noncoding sequences for production of a NA viral segment and does not include sequence for mRNA production of NA, and wherein if the host cell has a transcription cassette for eight viral segments, at least one of the segments is modified so that a functional influenza virus protein is not expressed from that segment and wherein the modified segment is not the PB2 segment.

11. The host cell of claim 10 which has 1, 2, 3, 4, 5, 6, or 7 of the expression cassettes for production of viral segments.

12. The host cell of claim 10 which stably expresses one or more of the transcription cassettes for mRNA production.

13. The host cell of claim 10 further comprising a transcription cassette comprising a promoter linked to 5' influenza virus sequences comprising 5' influenza virus noncoding sequences linked to a DNA of interest linked to Y influenza virus sequences comprising 3' influenza virus noncoding sequences linked to a transcription termination sequence.

\* \* \* \* \*

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: A synthetic peptide

<400> SEQUENCE: 1

Thr Tyr Gln Arg Thr Arg Ala Leu Val
1               5

<210> SEQ ID NO 2
<211> LENGTH: 9
<212> TYPE: PRT
<213> ORGANISM: Artificial Sequence
<220> FEATURE:
<223> OTHER INFORMATION: A synthetic peptide

<400> SEQUENCE: 2

Ile Tyr Ser Thr Val Ala Ser Ser Leu
1               5